(12) United States Patent
Munroe et al.

(10) Patent No.: US 6,566,096 B2
(45) Date of Patent: May 20, 2003

(54) MAMMALIAN EDG-7 RECEPTOR HOMOLOGS

(75) Inventors: Donald G. Munroe, Waterdown (CA); Ashwani K. Gupta, Mississauga (CA); Roman L. Zastawny, Etobicoke (CA)

(73) Assignee: NPS Allelix Corp., Mississauga (CA)

( * ) Notice: Subject to any disclaimer, the term of this patent is extended or adjusted under 35 U.S.C. 154(b) by 0 days.

(21) Appl. No.: 09/731,030

(22) Filed: Dec. 7, 2000

(65) Prior Publication Data

US 2002/0142375 A1 Oct. 3, 2002

Related U.S. Application Data

(63) Continuation of application No. 09/221,851, filed on Dec. 29, 1998, now abandoned.
(60) Provisional application No. 60/070,184, filed on Dec. 30, 1997.

(51) Int. Cl.$^7$ .................. C07K 14/705; C12N 15/12
(52) U.S. Cl. .............. 435/69.1; 435/252.3; 435/320.1; 530/350; 536/23.5
(58) Field of Search .................. 435/69.1, 252.3, 435/320.1; 530/350; 536/23.5

(56) References Cited

U.S. PATENT DOCUMENTS 6,060,272 A * 5/2000 Li et al. .................. 435/69.1

FOREIGN PATENT DOCUMENTS

| WO | WO97/00952 | 1/1997 |
| WO | WO98/48016 | 10/1998 |
| WO | WO98/50549 | 11/1998 |
| WO | WO99/35106 | 7/1999 |

OTHER PUBLICATIONS

Lado, et al., *Cloning of the Rat EDG–1 Immediate–Early Gene; Expression Pattern Suggests Diverse Functions;* Gene 149(2):331–336 (1994).
GenBank No. AA51451, Marra, et al. (Jun. 1997).
GenBank No. AA254425, Marra et al. (Mar. 1997).
Levitt et al., *Mapping of the Gene for Hormone Sensitive Lipase (LIPE) to Chromosome 19q13.1→q13.2*, Cytogenet Cell Genet 69:211–214(1995).
An et al., *Molecular Cloning of the Human EDG2 Protein and Its Identification as a Functional Cellular Receptor for Lysophosphatidic Acid*, Biochemical and Biophysical Research Communication, vol. 231, pp. 619–622 (1997).
Yamaguchi et al., *Molecular Cloning of the Novel Human G Protein–Coupled Receptor (GPCR) Gene Mapped on Chromosome 9*, Biochemical and Biophysical Research Communication, vol. 227 (1996), pp. 608–614.
Gräler, et al., *EDG6, a Novel G–Protein–Coupled Receptor Related to Receptors for Bioactive Lysophospholipids, is Specifically Expressed in Lymphoid Tissue*, Genomics 53, pp. 164–169 (1998).

* cited by examiner

Primary Examiner—John Ulm
(74) Attorney, Agent, or Firm—Rothwell, Figg, Ernst & Manbeck

(57) ABSTRACT

The present invention is directed to nucleic acid sequence and amino acid sequences for mammalian EDG-7 receptor homologs, and particularly for human EDG-7 receptor homologs. The invention also provides methods for determining agonists and antagonsits for EDG-7 receptors in addition to assays, expression vectors, host cells and methods for treating disorders associated with abherrent expression or activity of EDG-7.

5 Claims, 17 Drawing Sheets

FIGURE 1A

Human edg-7 sequence derived from BAC clone 460D20 (Genome Systems control no. 18241) and PAC clone 230F18 (control no. 19520). Translation starts at nt 16 and ends with a stop codon at nt 1168-1170. Translation initiation and termination codons are underlined below.

```
   1  CCCCCGGGGG AGGCCATGAA CGCCACGGGG ACCCCGGTGG CCCCCGAGTC
  51  CTGCCAACAG CTGGCGGCCG GCGGGCACAG CCGGCTCATT GTTCTGCACT
 101  ACAACCACTC GGGCCGGCTG GCCGGCGCG  GGGGCCGGA  GGATGGCGGC
 151  CTGGGGGCCC TGCGGGGGCT GTCGGTGGCC GCCAGCTGCC TGGTGGTGCT
 201  GGAGAACTTG CTGGTGCTGG CGGCCATCAC CAGCCACATG CGGTCGCGAC
 251  GCTGGGTCTA CTATTGCCTG GTGAACATCA CGCTGAGTGA CCTGCTCACG
 301  GGCGCGGCCT ACCTGGCCAA CGTGCTGCTG TCGGGGCCC  GCACCTTCCG
 351  TCTGGCGCCC GCCCAGTGGT TCCTACGGGA GGGCCTGCTC TTCACCGCCC
 401  TGGCCGCCTC CACCTTCAGC CTGCTCTTCA CTGCAGGGGA GCGCTTTGCC
 451  ACCATGGTGC GGCCGGTGGC CGAGAGCGGG GCCACCAAGA CCAGCCGCGT
 501  CTACGGCTTC ATCGGCCTCT GCTGGCTGCT GGCCGCGCTG CTGGGGATGC
 551  TGCCTTTGCT GGGCTGGAAC TGCCTGTGCG CCTTTGACCG CTGCTCCAGC
 601  CTTCTGCCCC TCTACTCCAA GCGCTACATC CTCTTCTGCC TGGTGATCTT
 651  CGCCGGCGTC CTGGCCACCA TCATGGGCCT CTATGGGGCC ATCTTCCGCC
 701  TGGTGCAGGC CAGCGGGCAG AAGGCCCCAC GCCCAGCGGC CCGCCGCAAG
 751  GCCCGCCGCC TGCTGAAGAC GGTGCTGATG ATCCTGCTGG CCTTCCTGGT
 801  GTGCTGGGGC CCACTCTTCG GCTGCTGCT  GGCCGACGTC TTTGGCTCCA
 851  ACCTCTGGGC CCAGGAGTAC CTGCGGGGCA TGGACTGGAT CCTGGCCCTG
 901  GCCGTCCTCA ACTCGGCGGT CAACCCCATC ATCTACTCCT TCCGCAGCAG
 951  GGAGGTGTGC AGAGCCGTGC TCAGCTTCCT CTGCTGCGGG TGTCTCCGGC
1001  TGGGCATGCG AGGGCCCGGG GACTGCCTGG CCCGGGCCGT CGAGGCTCAC
1051  TCCGGAGCTT CCACCACCGA CAGCTCTCTG AGGCCAAGGG ACAGCTTTCG
1101  CGGCTCCCGC TCGCTCAGCT TTCGGATGCG GGAGCCCCTG TCCAGCATCT
1151  CCAGCGTGCG GAGCATCTGA AGTTGCAGTC TTGCGTGTGG ATGGTGCAGC
1201  CACCGGGTGC GTGCCAGGCA GGCCCTCCTG GGGTACAGGA AGCTGTGTGC
1251  ACGCAGCCTC GCCTGTATGG GGAGCAGGGA ACGGGACAGG CCCCCATGGT
1301  CTTCCCGGTG GCCTCTCGGG GCTTCTGACG CCAAATGGGC TTCCCATGGT
1351  CACCCTGGAC AAGGAGGCAA CCACCCCACC TCCCCGTAGG AGCAGAGAGC
1401  ACCTGGTGT  GGGGGCGAGT GGGTTCCCCA CAACCCCGCT TCTGTGTGAT
1451  TCTGGGGAAG TCCCGGCCCC TCTCTGGGCC TCAGTAGGGC TCCCAGGCTG
1501  CAAGGGGTGG ACTGTGGGAT GCATGCCCTG GCAACATTGA AGTTCGATCA
```

FIGURE 1B

```
1551  TGGTACGTGA TGTTGCGGCC TCTTATTCCC TGGTGCGTGC ATGTGTGGGG
1601  GCCGTGGCTC AGGGGGGCTG TGGATCTAGG GGCAGCCGGG TGTGTCTTTG
1651  CTAGAGAGGG CCACGGGCCA GTGCCCTGTG AGGGTGGAGA GTGTGTGTGT
1701  GTGTGTGTGT GTGTGTGTGG ACAACYTCTG GGCGTTGCGG GAAGTGGGGG
1751  TGACAATGAC AGTTAATGCC GCTCTTCTTG TTCACTTCCC CTTTAGAAAT
1801  GGCAGGGCCC ATGCCCATC TCTGGCYTCT GCATCTTTTG GGACCCACT
1851  CTCTGGGGCT GGCAGAGGCA CCACCTTGGC TTCCTGGGCT GGGGGAATCT
1901  TCCCTCACAT CCCCTTCAGC ATGAACGGCC TCGGCTTTCC CGGTGGGTAA
1951  AACAGTTTAA TCACTGAAGC CGAAGCACAG GGTTGATGGT ACACGCTCCC
2001  CGCCAGCCAC AGGGGCTGAC GACTGCCTGC CCCGTGAAAC TCCAGTGGAG
2051  ACGTTTCAGC TCCACACCAT TCAGTATGGG AGACGCCAGC CCCACGGGGC
2101  TACGGTGCAA GCAGATAACT GAATTTCGAA GTGTAGGTTG TGTTTAATTT
2151  GAATCTGTTT ATATTTCGGT AGCCCCATGG GGCGGGTGGG GGGGATCCAC
2201  TAGTTCTAGA GCGGCCGCCA CCGCGGTGGA GCTCCAGYWT TWGWTCCCKT
2251  TAGTGAGGGT TAATTGCGCG
```

FIGURE 2A

Sequence of the cDNA insert of clone pc3-hedg7#M10. Translation starts at nt 13 and ends with a stop codon at nt 1165-1167.

hedg7#M10.seq  Length: 1176

```
  1  AAGCTTGCCA CCATGAACGC CACGGGGACC CCGGTGGCCC CCGAGTCCTG

51  CCAACAGCTG GCGGCCGGCG GGCACAGCCG GCTCATTGTT CTGCACTACA

101  ACCACTCGGG CCGGCTGGCC GGGCGCGGGG GGCCGGAGGA TGGCGGCCTG

151  GGGGCCCTGC GGGGGCTGTC GGTGGCCGCC AGCTGCCTGG TGGTGCTGGA

201  GAACTTGCTG GTGCTGGCGG CCATCACCAG CCACATGCGG TCGCGACGCT

251  GGGTCTACTA TTGCCTGGTG AACATCACGC TGAGTGACCT GCTCACGGGC

301  GCGGCCTACC TGGCCAACGT GCTGCTGTCG GGGGCCCGCA CCTTCCGTCT

351  GGCGCCCGCC CAGTGGTTCC TACGGGAGGG CCTGCTCTTC ACCGCCCTGG

401  CCGCCTCCAC CTTCAGCCTG CTCTTCACTG TAGGGGAGCG CTTTGCCACC

451  ATGGTGCGGC CGGTGGCCGA GAGCGGGGCC ACCAAGACCA GCCGCGTCTA

501  CGGCTTCATC GGCCTCTGCT GGCTGCTGGC CGCGCTGCTG GGGATGCTGC

551  CTTTGCTGGG CTGGAACTGC CTGTGCGCCT TGACCGCTG CTCCAGCCTT

601  CTGCCCCTCT ACTCCAAGCG CTACATCCTC TTCTGCCTGG TGATCTTCGC

651  CGGCGTCCTG GCCACCATCA TGGGCCTCTA TGGGGCCATC TTCCGCCTGG

701  TGCAGGCCAG CGGGCAGAAG GCCCCACGCC AGCGGCCCG CCGCAAGGCC
```

FIGURE 2B

751  CGCCGCCTGC TGAAGACGGT GCTGATGATC CTGCTGGCCT TCCTGGTGTG

801  CTGGGGCCCA CTCTTCGGGC TGCTGCTGGC CGACGTCTTT GGCTCCAACC

851  TCTGGGCCCA GGAGTACCTG CGGGGCATGG ACTGGATCCT GGCCCTGGCC

901  GTCCTCAACT CGGCGGTCAA CCCCATCATC TACTCCTTCC GCAGCAGGGA

951  GGTGTGCAGA GCCGTGCTCA GCTTCCTCTG CTGCGGGTGT CTCCGGCTGG

1001 GCATGCGAGG GCCCGGGGAC TGCCTGGCCC GGGCCGTCGA GGCTCACTCC

1051 GGAGCTTCCA CCACCGACAG CTCTCTGAGG CCAAGGGACA GCTTTCGCGG

1101 CTCCCGCTCG CTCAGCTTTC GGATGCGGGA GCCCCTGTCC AGCAGCTCCA

1151 GCGTGCGGAG CATCTGAAGT TCTAGA

FIGURE 3

Predicted amino acid sequence of the HEDG7 polypeptide.

```
1    MNATGTPVAP ESCQQLAAGG HSRLIVLHYN HSGRLAGRGG PEDGGLGALR
51   GLSVAASCLV VLENLLVLAA ITSHMRSRRW VYYCLVNITL SDLLTGAAYL
101  ANVLLSGART FRLAPAQWFL REGLLFTALA ASTFSLLFTA GERFATMVRP
151  VAESGATKTS RVYGFIGLCW LLAALLGMLP LLGWNCLCAF DRCSSLLPLY
201  SKRYILFCLV IFAGVLATIM GLYGAIFRLV QASGQKAPRP AARRKARRLL
251  KTVLMILLAF LVCWGPLFGL LLADVFGSNL WAQEYLRGMD WILALAVLNS
301  AVNPIIYSFR SREVCRAVLS FLCCGCLRLG MRGPGDCLAR AVEAHSGAST
351  TDSSLRPRDS FRGSRSLSFR MREPLSSISS VRSI
```

FIGURE 4

Amino acid sequence of HEDG7 from expression clone pc3-hedg7#M10. The polypeptide product of pc3-hedg7#M10 was deduced from the sequence of the cDNA insert, and this variant of HEDG7 was designated HEDG7#M10.

```
  1  MNATGTPVAP ESCQQLAAGG HSRLIVLHYN HSGRLAGRGG PEDGGLGALR

51  GLSVAASCLV VLENLLVLAA ITSHMRSRRW VYYCLVNITL SDLLTGAAYL

101  ANVLLSGART FRLAPAQWFL REGLLFTALA ASTFSLLFTV GERFATMVRP

151  VAESGATKTS RVYGFIGLCW LLAALLGMLP LLGWNCLCAF DRCSSLLPLY

201  SKRYILFCLV IFAGVLATIM GLYGAIFRLV QASGQKAPRP AARRKARRLL

251  KTVLMILLAF LVCWGPLFGL LLADVFGSNL WAQEYLRGMD WILALAVLNS

301  AVNPIIYSFR SREVCRAVLS FLCCGCLRLG MRGPGDCLAR AVEAHSGAST

351  TDSSLRPRDS FRGSRSLSFR MREPLSSSSS VRSI.
```

FIGURE 5A

Alignment of human edg-7#M10 DNA sequence (clone pc3-hedg7#m10) with the encoded HEDG7#M10 polypeptide.

```
 13 ATGAACGCCACGGGGACCCCGGTGGCCCCCGAGTCCTGCCAACAGCTGGC  62
    ||||||||||||||||||||||||||||||||||||||||||||||||||
  1 MetAsnAlaThrGlyThrProValAlaProGluSerCysGlnGlnLeuAl  17

63 GGCCGGCGGGCACAGCCGGCTCATTGTTCTGCACTACAACCACTCGGGCC  112
    ||||||||||||||||||||||||||||||||||||||||||||||||||
 18 aAlaGlyGlyHisSerArgLeuIleValLeuHisTyrAsnHisSerGlyA  34

113 GGCTGGCCGGGCGCGGGGGGCCGGAGGATGGCGGCCTGGGGGCCCTGCGG  162
    ||||||||||||||||||||||||||||||||||||||||||||||||||
 35 rgLeuAlaGlyArgGlyGlyProGluAspGlyGlyLeuGlyAlaLeuArg  50

163 GGGCTGTCGGTGGCCGCCAGCTGCCTGGTGGTGCTGGAGAACTTGCTGGT  212
    ||||||||||||||||||||||||||||||||||||||||||||||||||
 51 GlyLeuSerValAlaAlaSerCysLeuValValLeuGluAsnLeuLeuVa  67

213 GCTGGCGGCCATCACCAGCCACATGCGGTCGCGACGCTGGGTCTACTATT  262
    ||||||||||||||||||||||||||||||||||||||||||||||||||
 68 lLeuAlaAlaIleThrSerHisMetArgSerArgArgTrpValTyrTyrC  84

263 GCCTGGTGAACATCACGCTGAGTGACCTGCTCACGGGCGCGGCCTACCTG  312
    ||||||||||||||||||||||||||||||||||||||||||||||||||
 85 ysLeuValAsnIleThrLeuSerAspLeuLeuThrGlyAlaAlaTyrLeu  100

313 GCCAACGTGCTGCTGTCGGGGGCCCGCACCTTCCGTCTGGCGCCCGCCCA  362
    ||||||||||||||||||||||||||||||||||||||||||||||||||
101 AlaAsnValLeuLeuSerGlyAlaArgThrPheArgLeuAlaProAlaGl  117

363 GTGGTTCCTACGGGAGGGCCTGCTCTTCACCGCCCTGGCCGCCTCCACCT  412
    ||||||||||||||||||||||||||||||||||||||||||||||||||
```

FIGURE 5B

```
118 nTrpPheLeuArgGluGlyLeuLeuPheThrAlaLeuAlaAlaSerThrP 134

413 TCAGCCTGCTCTTCACTGTAGGGGAGCGCTTTGCCACCATGGTGCGGCCG 462
    ||||||||||||||||||||||||||||||||||||||||||||||||||
135 heSerLeuLeuPheThrValGlyGluArgPheAlaThrMetValArgPro 150

463 GTGGCCGAGAGCGGGGCCACCAAGACCAGCCGCGTCTACGGCTTCATCGG 512
    ||||||||||||||||||||||||||||||||||||||||||||||||||
151 ValAlaGluSerGlyAlaThrLysThrSerArgValTyrGlyPheIleGl 167

513 CCTCTGCTGGCTGCTGGCCGCGCTGCTGGGGATGCTGCCTTTGCTGGGCT 562
    ||||||||||||||||||||||||||||||||||||||||||||||||||
168 yLeuCysTrpLeuLeuAlaAlaLeuLeuGlyMetLeuProLeuLeuGlyT 184

563 GGAACTGCCTGTGCGCCTTTGACCGCTGCTCCAGCCTTCTGCCCCTCTAC 612
    ||||||||||||||||||||||||||||||||||||||||||||||||||
185 rpAsnCysLeuCysAlaPheAspArgCysSerSerLeuLeuProLeuTyr 200

613 TCCAAGCGCTACATCCTCTTCTGCCTGGTGATCTTCGCCGGCGTCCTGGC 662
    ||||||||||||||||||||||||||||||||||||||||||||||||||
201 SerLysArgTyrIleLeuPheCysLeuValIlePheAlaGlyValLeuAl 217

663 CACCATCATGGGCCTCTATGGGGCCATCTTCCGCCTGGTGCAGGCCAGCG 712
    ||||||||||||||||||||||||||||||||||||||||||||||||||
218 aThrIleMetGlyLeuTyrGlyAlaIlePheArgLeuValGlnAlaSerG 234

713 GGCAGAAGGCCCCACGCCCAGCGGCCCGCCGCAAGGCCCGCCGCCTGCTG 762
    ||||||||||||||||||||||||||||||||||||||||||||||||||
235 lyGlnLysAlaProArgProAlaAlaArgArgLysAlaArgArgLeuLeu 250

763 AAGACGGTGCTGATGATCCTGCTGGCCTTCCTGGTGTGCTGGGCCCACT 812
    ||||||||||||||||||||||||||||||||||||||||||||||||||
251 LysThrValLeuMetIleLeuLeuAlaPheLeuValCysTrpGlyProLe 267

813 CTTCGGGCTGCTGCTGGCCGACGTCTTTGGCTCCAACCTCTGGGCCCAGG 862
    ||||||||||||||||||||||||||||||||||||||||||||||||||
268 uPheGlyLeuLeuLeuAlaAspValPheGlySerAsnLeuTrpAlaGlnG 284
```

FIGURE 5C

```
 863 AGTACCTGCGGGGCATGGACTGGATCCTGGCCCTGGCCGTCCTCAACTCG  912
     ||||||||||||||||||||||||||||||||||||||||||||||||||
 285 luTyrLeuArgGlyMetAspTrpIleLeuAlaLeuAlaValLeuAsnSer  300

913 GCGGTCAACCCCATCATCTACTCCTTCCGCAGCAGGGAGGTGTGCAGAGC  962
     ||||||||||||||||||||||||||||||||||||||||||||||||||
 301 AlaValAsnProIleIleTyrSerPheArgSerArgGluValCysArgAl  317

963 CGTGCTCAGCTTCCTCTGCTGCGGGTGTCTCCGGCTGGGCATGCGAGGGC  1012
     ||||||||||||||||||||||||||||||||||||||||||||||||||
 318 aValLeuSerPheLeuCysCysGlyCysLeuArgLeuGlyMetArgGlyP  334

1013 CCGGGGACTGCCTGGCCCGGGCCGTCGAGGCTCACTCCGGAGCTTCCACC  1062
     ||||||||||||||||||||||||||||||||||||||||||||||||||
 335 roGlyAspCysLeuAlaArgAlaValGluAlaHisSerGlyAlaSerThr  350

1063 ACCGACAGCTCTCTGAGGCCAAGGGACAGCTTTCGCGGCTCCCGCTCGCT  1112
     ||||||||||||||||||||||||||||||||||||||||||||||||||
 351 ThrAspSerSerLeuArgProArgAspSerPheArgGlySerArgSerLe  367

1113 CAGCTTTCGGATGCGGGAGCCCCTGTCCAGCAGCTCCAGCGTGCGGAGCA  1162
     ||||||||||||||||||||||||||||||||||||||||||||||||||
 368 uSerPheArgMetArgGluProLeuSerSerSerSerSerValArgSerI  384

Comparison of HEDG7#M10 with HEDG7 polypeptide predicted from the genomic DNA sequence. In HEDG7#M10, two amino acid substitutions relative to HEDG7 encoded by genomic DNA are found at positions 140 and 378 (*bold, underlined*).

```
              1                                                      50
HEDG7#M10    MNATGTPVAP ESCQQLAAGG HSRLIVLHYN HSGRLAGRGG PEDGGLGALR
    HEDG7    MNATGTPVAP ESCQQLAAGG HSRLIVLHYN HSGRLAGRGG PEDGGLGALR 51                                                     100
HEDG7#M10    GLSVAASCLV VLENLLVLAA ITSHMRSRRW VYYCLVNITL SDLLTGAAYL
    HEDG7    GLSVAASCLV VLENLLVLAA ITSHMRSRRW VYYCLVNITL SDLLTGAAYL 101                                                     150
HEDG7#M10    ANVLLSGART FRLAPAQWFL REGLLFTALA ASTFSLLFT$\underline{\textbf{V}}$ GERFATMVRP
    HEDG7    ANVLLSGART FRLAPAQWFL REGLLFTALA ASTFSLLFTA GERFATMVRP 151                                                     200
HEDG7#M10    VAESGATKTS RVYGFIGLCW LLAALLGMLP LLGWNCLCAF DRCSSLLPLY
    HEDG7    VAESGATKTS RVYGFIGLCW LLAALLGMLP LLGWNCLCAF DRCSSLLPLY 201                                                     250
HEDG7#M10    SKRYILFCLV IFAGVLATIM GLYGAIFRLV QASGQKAPRP AARRKARRLL
    HEDG7    SKRYILFCLV IFAGVLATIM GLYGAIFRLV QASGQKAPRP AARRKARRLL 251                                                     300
HEDG7#M10    KTVLMILLAF LVCWGPLFGL LLADVFGSNL WAQEYLRGMD WILALAVLNS
    HEDG7    KTVLMILLAF LVCWGPLFGL LLADVFGSNL WAQEYLRGMD WILALAVLNS 301                                                     350
HEDG7#M10    AVNPIIYSFR SREVCRAVLS FLCCGCLRLG MRGPGDCLAR AVEAHSGAST
    HEDG7    AVNPIIYSFR SREVCRAVLS FLCCGCLRLG MRGPGDCLAR AVEAHSGAST 351                                      385
HEDG7#M10    TDSSLRPRDS FRGSRSLSFR MREPLSS$\underline{\textbf{S}}$SS VRSI~
    HEDG7    TDSSLRPRDS FRGSRSLSFR MREPLSSISS VRSI~
```

FIGURE 7A

Multiple alignment of HEDG7 amino acid sequence with other edg family polypeptides, using the PILEUP (Wisconsin Package 9.0, Genetics Computer Group [GCG], Madison, Wisconsin) algorithm.

```
              1                                                    50
    Edg-2   MAAISTSIPV  ISQPQFTAMN  EPQCFYNESI  AFFYNRSGKH  LATEWN.TVS
    Edg-5   ~~~~~~~~~~  ~~~~~~~~~~  MNECHYDKHM  DFFYNRSNTD  TVDDWTGTKL
    Edg-1   ~~~~~MGPTS  VPLVKAHRSS  VSDYVNYDII  VRHYNYTGKL  .NISADKENS
    Edg-3   ~~~~~~~~~~  ~~MATALPPR  LQPVRGNETL  REHYQYVGKL  AGRLKEASEG
    Edg-4   ~~~~~~~~~~  ~~~~~~MGSL  YSEYLNPNKV  QEHYNYTKE.  .TLETQETTS
    Edg-7   ~~~~~MNATG  TPVAPESCQQ  LAAGGHSRLI  VLHYNHSGRL  AGRGGPEDGG 51                                                   100
    Edg-2   K.LVMGLGIT  VCIFIMLANL  LVMVAIYVNR  RFHFPIYYLM  ANLAAADFFA
    Edg-5   V.IVLCVGTF  FCLFIFFSNS  LVIAAVIKNR  KFHFPFYYLL  ANLAAADFFA
    Edg-1   IKLTSVVFIL  ICCFIILENI  FVLLTIWKTK  KFHRPMYYFI  GNLALSDLLA
    Edg-3   STLTTVLFLV  ICSFIVLENL  MVLIAIWKNN  KFHNRMYFFI  GNLALCDLLA
    Edg-4   RQVASAFIVI  LCCAIVVENL  LVLIAVARNS  KFHSAMYLFL  GNLAASDLLA
    Edg-7   LGALRGLSVA  ASCLVVLENL  LVLAAITSHM  RSRRWVYYCL  VNITLSDLLT 101                                                  150
    Edg-2   GLAYFYLMFN  TGPNTRRLTV  STWLLRQGLI  DTSLTASVAN  LLAIAIERHI
    Edg-5   GIAYVFLMFN  TGPVSKTLTV  NRWFLRQGLL  DSSLTASLTN  LLVIAVERHM
    Edg-1   GVAYTANLLL  SGATTYKLTP  AQWFLREGSM  FVALSASVFS  LLAIAIERYI
    Edg-3   GIAYKVNILM  SGKKTFSLSP  TVWFLREGSM  FVALGASTCS  LLAIAIERHL
    Edg-4   GVAFVANTLL  SGSVTLRLTP  VQWFAREGSA  FITLSASVFS  LLAIAIERHV
    Edg-7   GAAYLANVLL  SGARTFRLAP  AQWFLREGLL  FTALAASTFS  LLFTVGERFA 151                                                  200
    Edg-2   TVFR.MQLHT  RMSNRRVVVV  IVVIWTMAIV  MGAIPSVGWN  CICDIENCSN
    Edg-5   SIMR.MRVHS  NLTKKRVTLL  ILLVWAIAIF  MGAVPTLGWN  CLCNISACSS
    Edg-1   TMLK.MKLHN  GSNNFRLFLL  ISACWVISLI  LGGLPIMGWN  CISALSSCST
    Edg-3   TMIK.MRPYD  ANKRHRVFLL  IGMCWLIAFT  LGALPILGWN  CLHNLPDCST
    Edg-4   AIAK.VKLYG  SDKSCRMLLL  IGASWLISLV  LGGLPILGWN  CLGHLEACST
    Edg-7   TMVRPVAESG  ATKTSRVYGF  IGLCWLLAAL  LGMLPLLGWN  CLCAFDRCSS
```

FIGURE 7B

```
         201                                                              250
Edg-2    MAPLYSDSYL VFWAIFNLVT FVVMVVLYAH IFGYVRQRTM RMSRHSSGPR
Edg-5    LAPIYSRSYL VFWTVSNLMA FLIMVVVYLR IYVYVKRKTN VLSPHTSGSI
Edg-1    VLPLYHKHYI LFCTTVFTLL LLSIVILYCR IYSLVRTRSR RLTFRKNISK
Edg-3    ILPLYSKKYI AFCISIFTAI LVTIVILYAR IYFLVKSSSR KVANHNN...
Edg-4    VLPLYAKHYV LCVVTIFSII LLAVVALYVR IYCVVRSSHA DMA.......
Edg-7    LLPLYSKRYI LFCLVIFAGV LATIMGLYGA IFRLVQASGQ KAPRPAARRK 251                                                              300
Edg-2    RNR.DTMMSL LKTVVIVLGA FIICWTPGLV LLLLD.VCCP ..QCDVLAYE
Edg-5    SRR.RTPMKL MKTVMTVLGA FVVCWTPGLV VLLLDGLNCR ..QCGVQHVK
Edg-1    ASRSSENVAL LKTVIIVLSV FIACWAPLFI LLLLDV.GCK VKTCDILFRA
Edg-3    ...SERSMAL LRTVVIVVSV FIACWSPLFI LFLIDV.ACR VQACPILFKA
Edg-4    ...APQTLAL LKTVTIVLGV FIVCWLPAFS ILLLDY.ACP VHSCPILYKA
Edg-7    ARR......L LKTVLMILLA FLVCWGPLFG LLLADVFGSN LWAQEYLRGM 301                                                              350
Edg-2    KFFLLLAEFN SAMNPIIYSY RDKEMSATFR QILCCQRSEN PTGPTESSDR
Edg-5    RWFLLLALLN SVVNPIIYSY KDEDMYGTMK KMICCFSQEN PERRPSRIPS
Edg-1    EYFLVLAVLN SGTNPIIYTL TNKEMRRAFI RIMSC.CKCP SGDSAGKFKR
Edg-3    QWFIVLAVLN SAMNPVIYTL ASKEMRRAFF RLVCN.CLVR GRGARASPIQ
Edg-4    HYLFAVSTLN SLLNPVIYTW RSRDLRREVL RPL.Q.CWRP GVGVQGR.RR
Edg-7    DWILALAVLN SAVNPIIYSF RSREVCRAVL SFLCCGCLRL GMRGPGDCLA 351                                              399
Edg-2    SASSLNHTIL AGVHSNDHSV V~~~~~~~~~ ~~~~~~~~~~ ~~~~~~~~~
Edg-5    TVLSRSDTGS QYIEDSISQG AVCNKSTS~~ ~~~~~~~~~~ ~~~~~~~~~
Edg-1    PIIAGMEFSR SKSDNSSHPQ KDEGDNPETI MSSGNVNSSS ~~~~~~~~~
Edg-3    PALDPSRSKS SSSNNSSHSP KVKEDLPHTD PSSCIMDKNA ALQNGIFCN
Edg-4    GGTPGHHLLP LRSSSSLERG MHMPTSPTFL EGNTVV~~~~ ~~~~~~~~~
Edg-7    RAVEAHSGAS TTDSSLRPRD SFRGSRSLSF RMREPLSSSS SVRSI~~~~
```

FIGURE 8
Rat edg-7 partial genomic DNA sequence.

```
   1  CCGTGTGTAT GGCTGCATCG GTCTGTGCTG GCTGCTGGCA GCTACCCTGG
  51  GCCTGCTGCC CCTGCTGGGC TGGAACTGTG TGTGCGCCTT CCAGCGCTGC
 101  TCTAGCCTGC TGCCCCTCTA CTCCAAGGGC TATGtGCTCT TTTGTGTGGT
 151  GGTCTTCGCC CTAATCCTAG TGACTATCCT GAGCCTCTAC GGGGCCATCT
 201  TTAGGGTGGT CCGAGCCAAC GGGCAGAAGT CCCCGCGTCC TCCTGCCCGC
 251  CGCAAGTCCC GCAGGCTACT CAACACCGTG CTGATGATCT TGGTGGCTTT
 301  TGTGGTGTGC TGGGGTCCCC TGTTTGGCCT GCTCCTGGCC GACATCTTTG
 351  GATCTAATGT CTGGGCCCAG GAGTACCTGC GCGGCATGGA CTGGATCCTG
 401  GCCCTAGCTG TGCTCAACTC AGCCATCAAT CCTCTCATCT ATTCCTTCCG
 451  CAGCCGTGAG GTGCAGCACG CTGTGCTGAC CTTCCTGTGC TGCGGCTGCC
 501  TCAGGTTAGG CCTGAGAGGC CctGGAgACT GCCTGACCCG GATCACCGAG
 551  GCCcACTcTG GGCATCCAC CACTGACAGC TCGCTgAGGC CcAGGGAAAG
 601  TTTTCGGAcT TCGAGGTCAC TCaGCTTCAA gAtGCGAgAg CCGCTGTCCA
 651  GCGTTTCCAG CATCCCAGCG CCTAGAGCTT GAAcCAgCCG GTCGCCCACC
 701  GAGCAGGCCT CCCAGGAAAA GTTAARAAGG ACtGGAMACA AGATCTYAGC
 751  CGACAGTGAY TGARAAATGC TTGCAGGCCC CGGGTTCYTT CCACGAAAYT
 801  CCCCATGATG AATGTTYGGC AGGRAKKGCC AGATCCAGAT CCAGTGAGTC
 851  TGGGCCTCGA TGGGCTCCC AGGCAGCAAA GGGGGTKTCC ATKTCCGAGG
 901  CCATGGACGG GACAGGGCCT TACGGYTATT TCTTAGACAC AHKTKTKCTG
 951  CKACCAGGAY GCTGYAACAT GTCTCTTGGT CACAGTGCTT TGGGGGTGTG
1001  TCACTGGCAC ACAGTGCTTC GGGAGTGTGC TGGGAWGGGG TACACCTGCA
1051  CCATTTGTTY GAAGACAACC WGAHGYGTYG TAAGAACTAC AGGAGGGGCT
1101  GGGGGCACCC CAGTCTGTCA TCCATTCCTC TTCTCAGTGA CTTCCCCAKT
1151  GGGACAAGCA ACCTGCCCCC ATGGCCTCTC TCCTCCGGGT TCTCTATCTC
1201  TCTGTGGGGA GATAGACCCA CCCACCCGAG GTCTGGGCA ATCTCAACTG
1251  GTCATGTAAC CCTACAGCCT CGCCCTTCCG GTTMTGAATC ACCAAGATAT
1301  GCTGYGACAG GAAGCTGTGG ACTCXTACCT YGTGACAGTA CAG
```

FIGURE 9

Rat EDG-7 partial amino acid sequence.

TRANSLATE of: redg7.seq check: 1095 from: 2 to: 673
generated symbols 1 to: 224.

redg7.pep  Length: 224  December 19, 1997 17:07  Type: P  Check: 1302

```
  1   RVYGCIGLCW LLAATLGLLP LLGWNCVCAF QRCSSLLPLY SKGYVLFCVV
 51   VFALILVTIL SLYGAIFRVV RANGQKSPRP PARRKSRRLL NTVLMILVAF
101   VVCWGPLFGL LLADIFGSNV WAQEYLRGMD WILALAVLNS AINPLIYSFR
151   SREVQHAVLT FLCCGCLRLG LRGPGDCLTR ITEAHSGAST TDSSLRPRES
201   FRTSRSLSFK MREPLSSVSS IPAP
```

MAMMALIAN EDG-7 RECEPTOR HOMOLOGS

This is a continuation application of U.S. Patent application Ser. No. 09/221,851, filed on Dec. 29, 1998, now abandoned, which claims the benefit of application Ser. No. 60/070,184, Dec. 30, 1997 the disclosure of which is hereby incorporated by reference.

FIELD OF THE INVENTION

The present invention is in the field of molecular biology; more particularly, the present invention describes nucleic acid sequences and amino acid sequences for mammalian EDG-7 receptor homologs, and particularly for human EDG-7 receptor homologs.

BACKGROUND OF THE INVENTION

The family of edg receptors are commonly grouped with orphan receptors because their endogenous ligands are not known (for example see Hla T and Maciag T (1990) J Biol. Chem. 265:9308–13; U.S. Pat. No. 5,585,476). Recently, however, lysophospatidic acid has been demonstrated to be the endogenous ligand for the edg-2 receptor (Hecht et al. (1996) J. Cell. Biol. 135: 1071–1083; An et al. (1997) Biochem. Biophys. Res. Comm. 213: 619–622).

The edg family of receptors is seven transmembrane G protein coupled receptors (T7Gs or GPCRs). T7Gs are so named because of their seven hydrophobic domains that span the plasma membrane and form a bundle of antiparallel α helices. These transmembrane segments (TMS) are designated by roman numerals I–VII and account for structural and functional features of the receptor. In most cases, the bundle of helices forms a binding pocket; however, when the binding site must accommodate more bulky molecules, the extracellular N-terminal segment or one or more of the three extracellular loops participate in binding and in subsequent induction of conformational change in intracellular portions of the receptor. Specifically: the TM-VII is generally a highly conserved portion of the T7G receptors, and is often critically involved in ligand binding and receptor activation; the intracellular carboxy-terminal is involved in interactions with intracellular proteins, including those that transduce intracellular signals upon receptor activations; the carboxy-terminal is usually hydrophilic and highly antigenic relative to the receptor polypeptide as a whole and shows greatly reduced conservation.

Once the receptor is activated, the receptor, in turn, interacts with an intracellular G-protein complex which mediates further intracellular signaling activities, including: generally, the production of second messengers such as cyclic AMP (cAMP), phospholipase C, inositol triphosphate; activation of protein kinases; and alteration in the expression of specific genes.

T7G receptors are expressed and activated during numerous developmental and disease processes. Identification of a novel T7G receptor provides the opportunity to diagnose or intervene in such processes, and the receptor can he used in screening assays to identify physiological or pharmaceutical molecules which trigger, prolong or inhibit its activity or differentially modulate distinct intracellular pathways which are controlled from T7G receptors.

SUMMARY OF THE INVENTION

The invention provides isolated and unique nucleotide sequences that encode novel mammalian EDG-7 receptor homologs, and particularly, novel human EDG-7 (HEDG-7) receptor homologs. Herein, the nucleotide sequence encoding HEDG-7 is designated hedg-7.

The present invention also relates to the isolated and unique nucleotide sequences of the complement of hedg-7 mRNA. In addition, the invention features nucleotide sequences, which hybridize under stringent conditions to hedg-7.

The present invention also relates to nucleotide sequences that encode fragments or portions of hedg-7, or complements thereof, in addition to expression vectors and host cells comprising such nucleotide sequences.

The present invention also provides amino acid fragments, particularly fragments in the TM-VII and carboxy-terminal domains that are useful as antibodies for HEDG-7.

Furthermore, the invention relates to the use of the nucleotide sequences of hedg-7 and the amino acid sequences of HEDG-7, or its variants, in the diagnosis or treatment of diseased cells and/or tissues associated with aberrant expression of hedg-7.

Additional aspects of the invention include the antisense DNA of hedg-7; cloning or expression vectors containing hedg-7; host cells or organisms transformed with expression vectors containing hedg-7; chromosomal localization of hedg-7; expression and tissue distribution of hedg-7; a method for the production and recovery of purified HEDG-7 from host cells; purified protein, HEDG-7, which can be used to identify inhibitors for the downregulation of signal transduction involving HEDG-7; and methods of screening for ligands of hedg-7 using transformed cells.

In particular, the present invention provides an isolated nucleotide sequence selected from the group consisting of:

(a) the nucleotide sequence comprising nucleotides 16–1170 of FIG. 1A;

(b) the nucleotide sequence comprising nucleotides 13–1167 of FIG. 1B;

(c) a nucleotide sequence with 70% sequence identity to (a) or (b), more preferably at least about 80–85% sequence identity, and even more preferably at least about 90% sequence identity, and most preferably at least about 95% sequence identity, and which nucleotide sequence hybridizes under stringent conditions to the nucleotide sequence of (a) or (b), respectively, or portions thereof;

(d) a nucleotide sequence which encodes the amino acid sequence of FIG. 2A; and (e) a nucleotide sequence which encodes the amino acid sequence of FIG. 2B.

There is also provided: expression vectors; host cells; purified amino acid sequences; complementary nucleic acid sequences; biologically active fragments; and hybridization probes, for such nucleotide sequences and their encoded amino acid sequences.

BRIEF DESCRIPTION OF THE DRAWINGS

FIG. 1A shows nucleotides 1–1550 of a nucleotide sequence of human edg-7 sequence (SEQ ID NO:10) derived from BAC clone 460D20 (Genome Systems Control Number 18241) and PAC clone 230F18 (Control Number 19520). Translation starts at nucleotide 16 and ends with a stop codon at nucleotides 1168–1170. Translation initiation and termination codons are underlined.

FIG. 1B shows nucleotides 1551–2270 of the nucleotide sequence of human edg-7 sequence (SEQ ID NO:10).

FIG. 2A shows nucleotides 1–750 of the nucleotide sequence (SEQ ID NO:12) of the cDNA insert of clone pc3-hedg7#M10 clone. Translation starts at nucleotide 13 and ends with a stop codon at nucleotides 1165–1167.

FIG. 2B shows nucleotides 751–1176 of the nucleotide sequence (SEQ ID NO:12) of the cDNA insert of clone pc3-hedg7#M10 clone.

FIG. 3 shows the predicted amino acid sequence (SEQ ID NO:11) encoded by hedg-7 of FIGS. 1A and 1B. The features of the HEDG-7 polypeptide are as follows:

1. Seven-transmembrane topology typical of G protein coupled receptors:
   N-ter extracellular domain: 1–49
   TM-1: 50–70
   IL-1: 71–81
   TM-2: 82–105
   EL-1: 106–124
   TM-3: 125–143
   IL-2: 144–163
   TM-4: 164–182
   EL-2: 183–199
   TM-5: 200–224
   IL-3: 225–250
   TM-6: 251–272
   EL-3: 273–285
   TM-7: 286–304
   C-ter intracellular domain: 305–384.
2. Potential N-glycosylation sites: N-2, N-30.
3. Potential phosphorylation sites: S-77, T-159, S-308, S-360, S-380.

FIG. 4 shows the amino acid sequence (SEQ ID NO:13) encoded by hedg7#M10 in FIGS. 2A and 2B. The polypeptide product of pc3-hedg7#M10 was deduced from the sequence of the cDNA insert, and this variant of HEDG-7 was designated HEDG7#M10.

FIG. 5A shows an alignment of nucleotides 13–412 of the nucleotide sequence (SEQ ID NO:12) of hedg-7#M10 aligned with the amino acid sequence (SEQ ID NO:13) of HEDG7#M10.

FIG. 5B shows an alignment of nucleotides 413–862 of SEQ ID NO:12 with a portion of the amino acid sequence of SEQ ID NO:13.

FIG. 5C shows an alignment of nucleotides 863–1164 of SEQ ID NO:12 with a portion of the amino acid sequence of SEQ ID NO:13.

FIG. 6 shows an alignment of the amino acid sequences of HEDG7#M10 (SEQ ID NO:13) and HEDG7 (SEQ ID NO:11). In SEQ ID NO:13, there are two amino acid substitutions relative to the HEDG-7 amino acid sequence of SEQ ID NO:11, found at positions 140 and 378 (bolded and underlined).

FIG. 7A shows a multiple alignment of the HEDG-7 predicted amino acid sequence of SEQ ID NO:13 with the amino acid sequences of other EDG receptors (EDG-2, SEQ ID NO:15; EDG-5, SEQ ID NO:16; EDG-1, SEQ ID NO:17; EDG-3, SEQ ID NO:18 and EDG-4, SEQ ID NO:19), using the PILEUP (Wisconsin Package 9.0, Genetics Computer Group, Madison, Wis.) algorithm.

FIG. 7B continues the multiple alignment of the HEDG-7 predicted amino acid sequence of SEQ ID NO:13 with the amino acid sequences of other EDG receptors (EDG-2, SEQ ID NO:15; EDG-5, SEQ ID NO:16; EDG-1, SEQ ID NO:17; EDG-3, SEQ ID NO:18 and EDG-4, SEQ ID NO:19), using the PILEUP algorithm.

FIG. 8 shows a partial genomic DNA sequence (SEQ ID NO:20) of rat edg-7.

FIG. 9 shows a predicted partial amino acid sequence (SEQ ID NO:21) of rat EDG-7.

Figure 10:
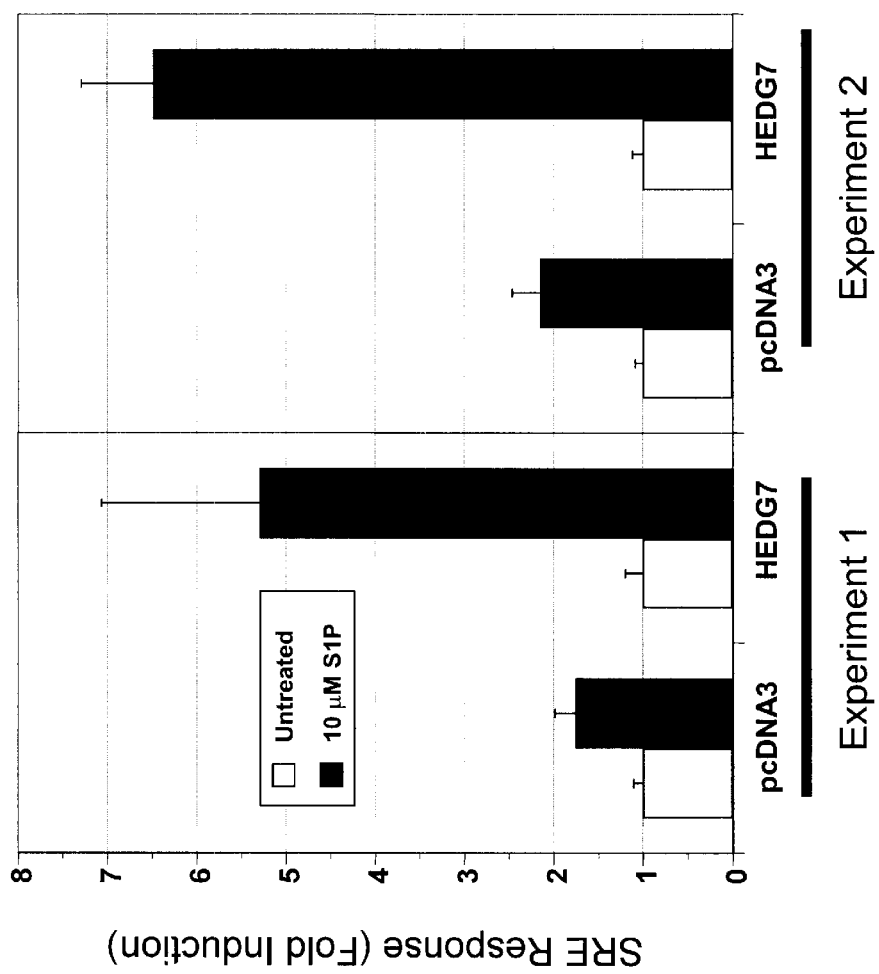

FIG. 10 is a bar graph showing the SRE response of a pcDNA3-HEDG7 clone to 10 $\mu$M S1P.

Figure 11:
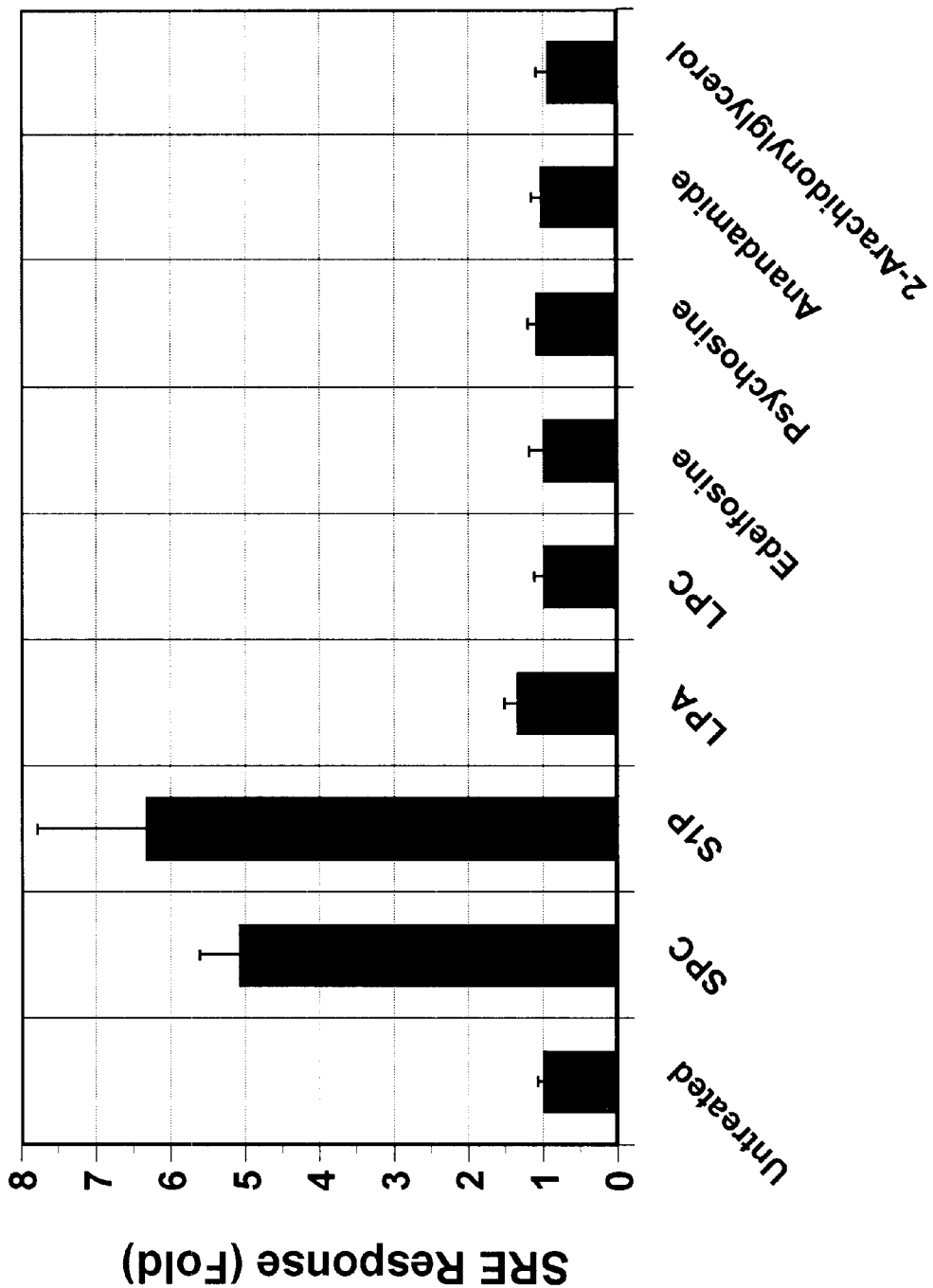

FIG. 11 is a bar graph showing the SRE response of 5 $\mu$M SPC, S1P, LPA, lysophosphatidylcholine (LPC), edelfosine, psychosine, anandamine or 2-arachidonylglycerol.

Figure 12:
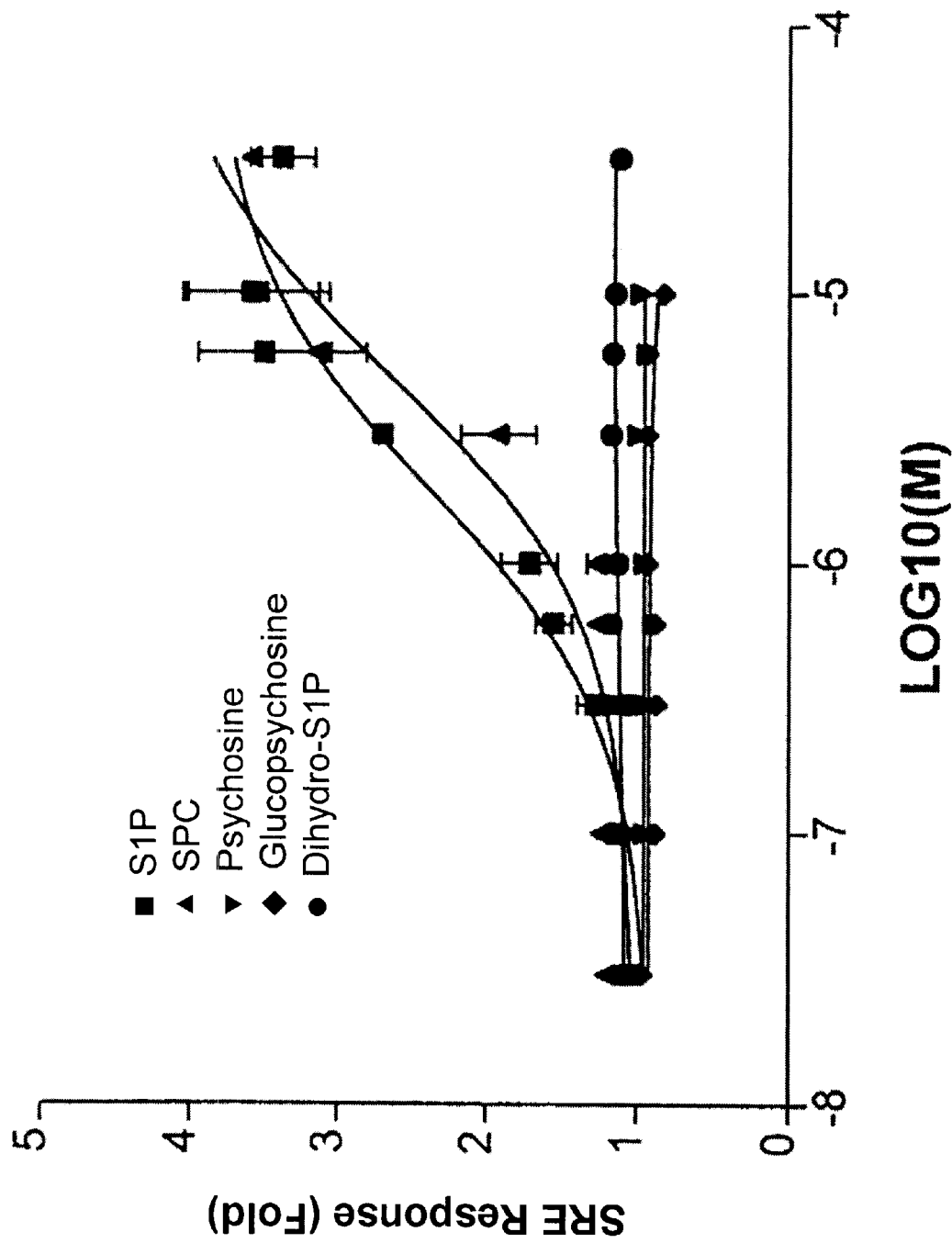

FIG. 12 is a graph showing the SRE dose response of S1P, SPC, psychosine, glucopsychosine and dihydrosphingosine 1-phosphate (dihydro-S1P).

DETAILED DESCRIPTION OF THE INVENTION

The invention relates in one respect to polynucleotides, in their isolated form, that encode the human edg-7 receptor. The EDG receptors are characterized by structural features common to the G-protein coupled receptor class, including seven transmembrane regions, and by the functional properties of binding lysophingolipids selectively. When expressed functionally in a host cell, i.e., in operable linkage with a responsive second messenger system the EDG-7 receptors are capable further of responding to lysophingolipid or binding by signal transduction. In this regard, the activity of HEDG-7 receptor can be measured using any of a variety of appropriate functional assays described hereinbelow.

As used herein and designated by the upper case abbreviation, HEDG-7, refers to a human EDG-7 receptor homolog in either naturally occurring or synthetic form. The HEDG-7 receptor is activated by S1P and SPC and includes the amino acid sequence of FIG. 3 or 4 and biologically active fragments thereof. More particularly, the HEDG-7 receptors preferably have at least 90% sequence identity with each other, and more preferably at least 95% sequence identity with each other.

All publications and patent applications mentioned herein are incorporated by reference for the purpose of describing the methodologies, cell lines and vectors, among other things. However, nothing herein is to be construed as an admission that the invention is not entitled to antedate such disclosure, for example, by virtue of prior invention.

Definitions

The following definitions are used herein for the purpose of describing particular terms used in the application. Any terms not specifically defined should be given the meaning commonly understood by one of ordinary skill in the art to which the invention pertains.

As used herein "isolated" means separated from nucleotide sequences that encode other proteins. In the context of polynucleotide libraries, for instance, a hedg-7 receptor-encoding nucleotide sequence is considered "isolated" when it has been selected, and hence removed from association with other nucleotide sequences within the library. Such nucleotide sequences may be in the form of RNA, or in the form of DNA including cDNA, genomic DNA and synthetic DNA.

As used herein "purified" refers to sequences that are removed from their natural environment, and are isolated or separated, and are at least 60% free, preferably 75% free, and most preferably 90% free from other components with which they are naturally associated.

An "oligonucleotide" is a stretch of nucleotide residues, which has a sufficient number of bases to be used as an oligomer, amplimer or probe in a polymerase chain reaction (PCR). Oligonucleotides are prepared from genomic or cDNA sequence and are used to amplify, reveal or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring, recombinant, or chemically synthesized single—or double—stranded nucleic acids or be chemically synthesized. They are useful in detecting the presence of identical or similar sequences.

A "portion" or "fragment" of a nucleotide or nucleic acid sequence comprises all or any part of the sequence having fewer nucleotides than about 6 kb, preferably fewer than about 1 kb. A portion or fragment can be used as a probe. Such probes may be labeled with reporter molecules using nick translation, Klenow fill-in reaction, PCR or other methods well known in the art. To optimize reaction conditions and to eliminate false positives, nucleic acid probes may be used in Southern, Northern or in situ hybridizations to determine whether DNA or RNA encoding HEDG-7 is present in a cell type, tissue, or organ.

"Reporter" molecules are those radionuclides, enzymes, fluorescent, chemiluminescent, or chromogenic agents which associate with, establish the presence of, and may allow quantification of a particular nucleotide or amino acid sequence.

"Recombinant nucleotide variants" encoding HEDG-7 may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Chimeric" molecules may be constructed by introducing all or part of the nucleotide sequence of this invention into a vector containing additional nucleic acid sequence which might be expected to change any one (or more than one) of the following HEDG-7 characteristics: cellular location, distribution, ligand-binding affinities, interchain affinities, degradation/turnover rate, signaling, etc.

"Biologically Active or Active" refers to those forms, fragments, or domains of any HEDG-7 polypeptide which retain at least some of the biological and/or antigenic activities of any naturally occurring HEDG-7.

"Naturally occurring HEDG-7" refers to a polypeptide produced by cells which have not been genetically engineered and specifically contemplates various polypeptides arising from post-translational modifications of the polypeptide including but not limited to acetylation, carboxylation, glycosylation, phosphorylation, lipidation and acylation.

"Derivative" refers to those amino acid sequences and nucleotide sequences which have been chemically modified. Such techniques for polypeptide derivatives include: ubiquitination; labeling (see above); pegylation (derivatization with polyethylene glycol); and chemical insertion or substitution of amino acids such as ornithine which do not normally occur in human proteins. A nucleotide sequence derivative would encode the amino acid which retains its essential biological characteristics of the natural molecule.

"Recombinant polypeptide variant" refers to any polypeptide which differs from naturally occurring HEDG-7 by amino acid insertions, deletions and/or substitutions, created using recombinant DNA techniques. Guidance in determining which amino acid residues may be replaced, added or deleted without abolishing activities of interest may be found by comparing the sequence of HEDG-7 with that of related polypeptides and minimizing the number of amino acid sequence changes made in highly conserved regions.

Amino acid "substitutions" are conservative in nature when they result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically or by systematically making insertions, deletions, or substitutions of nucleotides in the hedg-7 sequence using recombinant DNA techniques.

A "signal or leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and the same length as (or considerably shorter than) a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biological and/or antigenic activity.

"Inhibitor" is any substance which retards or prevents a biochemical, cellular or physiological reaction or response. Common inhibitors include but are not limited to antisense molecules, antibodies, and antagonists.

"Standard" is a quantitative or qualitative measurement for comparison. It is based on a statistically appropriate number of normal samples and is created to use as a basis of comparison when performing diagnostic assays, running clinical trials, or following patient treatment profiles.

"Stringent conditions" is used herein to mean conditions that allow for hybridization of substantially related nucleic acid sequences. Such hybridization conditions are described by Sambrook et al., Molecular Cloning: A Laboratory Manual, 2nd ed., Cold Spring Harbor Press, 1989. Generally, stringency occurs within a range from about 5° C. below the melting temperature of the probe to about 20° C.–25° C. below the melting temperature. As understood by ordinary skilled persons in the art, the stringency conditions may be altered in order to identify or detect identical or related nucleotide sequences. Factors such as the length and nature (DNA, RNA, base composition) of the sequence, nature of the target (DNA, RNA, base composition, presence in solution or immobilization, etc.) and the concentration of the salts and other componenets (e.g. the presence or absence of formamide, dextran sulfate and/or polyethylene glycol) are considered and the hybridization solution may be varied to generate conditions of either low or high stringency.

"Animal" as used herein may be defined to include human, domestic (cats dogs, etc.), agricultural (cows, horses, sheep, etc.) or test species (mouse, rat, rabbit, etc.).

"Nucleotide sequences" as used herein are oligonucleotides, polynucleotides, and fragments or portions thereof, and are DNA or RNA of genomic or synthetic origin which may be single or double stranded, and represent the sense or complement or antisense strands.

"Sequence Identity" is known in the art, and is a relationship between two or more polypeptide sequences or two or more polynucleotide sequences, as determined y comparing the sequences, particularly, as determined by the match between strings of such sequences. Sequence identity can be readily calculated by known methods (*Computational*

*Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). While there exist a number of methods to measure identity between two sequences, the term is well known to skilled artisans (see, for example, *Sequence Analysis in Molecular Biology; Sequence Analysis Primer;* and Carillo, H., and Lipman, D., SIAM *J. Applied Math.,* 48: 1073 (1988)). Methods commonly employed to determine identity between sequences include, but are not limited to those disclosed in Carillo, H., and Lipman, D., SIAM *J. Applied Math.,* 48: 1073 (1988) or, preferably, in Needleman and Wunsch, *J. Mol. Biol.,* 48: 443–445, 1970, wherein the parameters are as set in version 2 of DNASIS (Hitachi Software Engineering Co., San Bruno, Calif.). Computer programs for determining identity are publicly available. Preferred computer program methods to determine identity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990)). The BLASTX program is publicly available from NCBI (blast@ncbi.nlm.nih.gov) and other sources (BLAST Manual, Altschul, S., et al., NCBI NLM NIH Bethesda, Md. 20894; Altschul, S., et al., *J. Mol. Bio.* 215: 403–410 (1990)). Computational Molecular Biology, Lesk, A. M, ed. Unless specified otherwise in the claims, the percent identity for the purpose of interpreting the claims shall be calculated by the Needleman and Wucnsch algorithm with the parameters set in version 2 of DNASIS.

Phospholipids have been demonstrated to be important regulators of cell activity, including mitogenisis (Xu et al. (1995) J. Cell. Physiol., 163: 441–450) and apoptosis, cell adhesion and regulation of gene expression. Specifically, for example, LPA elicits growth factor-like effects on cell proliferation (Moolenar (1996) J. Biol. Chem, 270: 12949–12952) and cell migration (Imamura et al. (1993) Biochem. Biophys. Res. Comm., 193: 497–503). Further, considerable circumstantial evidence indicates that phospholipids may be involved in various disease states including cancer (Imamura et al., (1993) Biochem. Biophys. Res. Comm., 193: 497–503); diseases having an inflammatory component (Fourcade et al. (1995), Cell, 80(6): 919–927, including adult respiratory distress, neurodegeneration (Jalink et al. (1993) Cell Growth Differ., 4: 247–255), rheumatoid arthritis (Natiarajan et al. (1995) J. Lipid Res., 36(9): 2005–2016), psoriasis and inflammatory bowel disease. Thus, modulators of HEDG-7 expression or activity is likely to be useful in treatment or prevention of such disease states.

The edg receptor family of T7G receptors has been subdivided into 2 subgroups on the basis of sequence similarity and genomic organization (Chun, Contos & Munroe, in press). We have determined that edg-2, edg-5 (U.S. Ser. No. 08/997,803) and edg-6 (Genbank Accession AF011466) respond to LPA as an agonist, and share a common intron structure within their coding regions. Edg-1, edg-3 and edg-4/H218 (Accession U10699) have intronless coding regions and respond to S1P and SPC as agonists. The present T7G receptor, HEDG-7, has no intron within the coding region; however, its amino acid sequence shows motifs characteristic of both edg family subgroups. (See: FIG. 4)

One aspect of the present invention is a method for using recombinant HEDG-7 receptors in an assay for screening ligands and potential drug candidates. Although the use of T7G receptors in high-throughput screening is well-known, no such screen has been reported for the HEDG-7 receptor. More specifically, the novel HEDG-7 receptor presented herein can be used to identify and rank the relative potency and efficacy of potential agonists. These compounds may be useful inasmuch as they would be expected to modulate cellular or physiological responses to HEDG-7 agonists, or to initiate or supplement HEDG-7 signaling in cells where the receptor occurs. Equally, once a quantitative and reliable assay is established, it can readily be applied to identify and rank the relative potency and efficacy of receptor antagonists. This application, without limiting other aspects, of the screening methods described herein is specifically contemplated and incorporated within the scope of this invention.

It was determined that S1P and SPC are agonists for HEDG-7. (See FIGS. 7–9) On the other hand, it was determined that LPA, edelfosine, psychosine, glucosychosine, dihydro-S1P, anadamide and 2-arachidonylglycerol do not act as HEDG-7 agonists. (See FIGS. 8,9) Other HEDG-7 ligands are likely to be found among the phospholipid class of compounds Therefore, in one embodiment, phospholipid molecules could be screened to identify ligands. Particularly, it is believed that potential ligands include fatty acid chains of differing length, such as 16, 17, 18, 19, 20, 22 and 24 carbon units, with or without 1, 2, 3 or 4 unsaturated carbon—carbon bonds. Phosphatidic acid, sphingosine, numerous lysophospholipids and lysosphingolipids play roles in pathophysiology of human diseases. HEDG-7, by responding to low circulating or locally produced levels of such bioactive lipids, may initiate significant components of the pathophysiological response in such a disease. Edg-7 was not detected on a multi-tissue Northern blot, suggesting that high-level expression is not widespread in normal tissues. RT-PCR has demonstrated the presence in edg-7 mRNA in mammary gland and lymph node tissue. Further, RT-PCR, has demonstrated edg-7 RNA expression in several rat tissues, including colon, lung, spleen, hypothalamus, hindbrain, small intestine, liver and kidney. Edg-7 cDNA inserts have also been detected in human cDNA libraries synthesized from small intestine and fetal brain and may be expressed within specialized cell populations of these and other tissues.

The nucleotide sequences encoding HEDG-7 (or their complement) have numerous applications in techniques known to those skilled in the art of molecular biology. These techniques include use as hybridization probes, use in the construction of oligomers for PCR, use for chromosome and gene mapping, use in the recombinant production of HEDG-7, and use in generation of antisense DNA or RNA, their chemical analogs and the like. Uses of nucleotides encoding HEDG-7 disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of HEDG-7 encoding nucleotide sequences may be produced. Some of these will only bear minimal homology to the nucleotide sequence of the known and naturally occurring HEDG-7. The invention has specifically contemplated each and every possible variation-of nucleotide sequence that could be made by selecting combinations based on possible codon choices. These combinations are made in accordance with the standard triplet genetic code as applied to the nucleotide sequence of naturally occurring hedg-7, and all such variations are to be considered as being specifically disclosed.

Although the nucleotide sequences which encode HEDG-7, its derivatives or its variants are preferably capable of hybridizing to the nucleotide sequence of the naturally occurring hedg-7 under stringent conditions, it may be advantageous to produce nucleotide sequences encoding HEDG-7 or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding HEDG-7 and/or its derivatives without altering the encoded amino acid sequence include the production of RNA transcripts having more desirable properties, such as a greater half-life, than transcripts produced from the naturally occurring sequence.

Human genes often show considerable actual polymorphism; that is, variation in nucleotide sequence among a fraction of the entire human population. In many cases this polymorphism can result in one or more amino acid substitutions. While some of these substitutions show no demonstrable change in function of the protein, others may produce varying degrees of functional effects. In fact, many natural or artificially produced mutations can lead to expressible HEDG proteins. Each of these variants, whether naturally or artificially produced, is considered to be equivalent and specifically incorporated into the present invention.

Nucleotide sequences encoding HEDG-7 may be joined to a variety of other nucleotide sequences by means of well established recombinant DNA techniques (Sambrook J et al (1989) Molecular Cloning: A Laboratory Manual, Cold Spring Harbor Laboratory, Cold Spring Harbor N.Y.; or Ausubel F M et al (1989) Current Protocols in Molecular Biology, John Wiley & Sons, New York City). Useful nucleotide sequences for joining to hedg-7 include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for hedg-7 specific hybridization probes capable of hybridizing with naturally occurring nucleotide sequences encoding HEDG-7. Such probes may also be used for the detection of similar T7G encoding sequences and should preferably contain at least 60% nucleotide identity to hedg-7 sequence. The hybridization probes of the subject invention may be derived from the nucleotide sequence presented in the figures for hedg-7 or from genomic sequences including promoter, enhancers, introns or 3'-untranslated regions of the native gene. Hybridization probes may be labeled by a variety of reporter molecules using techniques well known in the art. Preferably, the hybridization probes incorporate at least 15 nucleotides, and preferably at least 25 nucleotides, of the hedg-5 receptor. Suitable hybridization probes would include: consensus fragments, for example, those regions of the rat and human edg-5 receptor that are identical; the extracellular edg-7 binding domain; the stipulated transmembrane regions and the C-terminal portion of the receptor.

It will be recognized that many deletional or mutational analogs of nucleic acid sequences for HEDG-7 will be effective hybridization probes for HEDG-7 nucleic acid. Accordingly, the invention relates to nucleic acid sequences that hybridize with such HEDG-7 encoding nucleic acid sequences under stringent conditions.

Stringent conditions will generally allow hybridization of sequence with at least about 70% sequence identity, more preferably at least about 80–85% sequence identity, even more preferably at least about 90% sequence identity, and most preferably with at least about 95% sequence identity Hybridization conditions and probes can be adjusted in well-characterized ways to achieve selective hybridization of human-derived probes. Nucleic acid molecules that will hybridize to HEDG-7 encoding nucleic acid under stringent conditions can be identified functionally, using methods outlined above, or by using for example the hybridization rules reviewed in Sambrook et al., Molecular Cloning: A Laboratory Manual, 2nd ed., Cold Spring Harbor Press, 1989. Without limitation, examples of the uses for hybridization probes include: histochemical uses such as identifying tissues that express HEDG-7; measuring mRNA levels, for instance to identify a sample's tissue type or to identify cells that express abnormal levels of HEDG-7; and detecting polymorphisms in the HEDG-7. RNA hybridization procedures are described in Maniatis et al. Molecular Cloning, a Laboratory Manual (Cold Spring Harbor Press, 1989). PCR as described U.S. Pat. Nos. 4,683,195; 4,800,195; and 4,965,188 provides additional uses for oligonucleotides based upon the nucleotide sequence which encodes the EDG-7 sequences of the invention. Such probes used in PCR may be of recombinant origin, chemically synthesized, or a mixture of both. Oligomers may comprise discrete nucleotide sequences employed under optimized conditions for identification of hedg-7 in specific tissues or diagnostic use. The same two oligomers, a nested set of oligomers, or even a degenerate pool of oligomers may be employed under less stringent conditions for identification of closely related DNA's or RNA's. Rules for designing PCR primers are now established, as reviewed by PCR Protocols, Cold Spring Harbor Press, 1991. Degenerate primers, i.e., preparations of primers that are heterogeneous at given sequence locations, can be designed to amplify nucleic acid sequences that are highly homologous to, but not identical to hedg-7. Strategies are now available that allow for only one of the primers to be required to specifically hybridize with a known sequence. See, Froman et al., Proc. Natl. Acad. Sci. USA 85: 8998, 1988 and Loh et al., Science 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified. PCR methods of amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, for example, PCR Protocols, Cold Spring Harbor Press, 1991.

Other means of producing specific hybridization probes for hedg-7 include the cloning of nucleic acid sequences encoding HEDG-7 or HEDG-7 derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

More particularly, a method for detection of polynucleotides that hybridize with hedg-7 is exemplified in Example 9, wherein a positive test correlates to approximately at least 70% identitiy, and more preferably at least 80–85% sequence identity.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with longer portion of an existing genomic or recombinant sequence.

The nucleotide sequence for hedg-7 can be used in an assay to detect inflammation or disease associated with abnormal levels of HEDG-7 expression. The cDNA can be labeled by methods known in the art, added to a fluid, cell or tissue sample from a patient, and incubated under hybridizing conditions. After an incubation period, the sample is washed with a compatible fluid which optionally contains a reporter molecule. After the compatible fluid is rinsed off, the reporter molecule is quantitated and compared with a standard as previously defined.

A diagnostic test for aberrant expression of HEDG-7 can accelerate diagnosis and proper treatment of abnormal conditions of for example, the heart, kidney, lung and testis. Specific examples of conditions in which aberrant expression of HEDG-7 may play a role include adult respiratory distress, asthma, rheumatoid arthritis, cardiac ischemia, acute pancreatitis, septic shock, psoriasis, acute cyclosporine nephrotoxicity and early diabetic glomerulopathy, as well as lung damage following exposure to cigarette smoke, asbestos or silica.

New nucleotide sequences can be assigned to chromosomal subregions by physical mapping. The mapping of new genes or nucleotide sequences provide useful landmarks for investigators searching for disease genes using positional cloning or other gene discovery techniques. Once a disease or syndrome, such as ataxia telangiectasia (AT), has been crudely localized by genetic linkage to a particular genomic region, for example, AT to 1 1q22–23 (Gatti et al (1988) Nature 336:577–580), any sequences mapping to that area may represent or reveal genes for further investigation. The nucleotide sequence of the subject invention may also be used to detect differences in gene sequence between normal and carrier or affected individuals.

The chromosomal localization of the hedg-7 gene was mapped to chromosome 19p13.3 by fluorescent in situ hybridization (FISH). This localization is nearly identical to the localizations of edg-6 and edg-4, as determined via FISH analysis with appropriate BAC or PAC DNA clones. Although the precise distances and relative orders of these three genes have not yet been determined, it raises the possibility of an edg gene cluster that may be maintained by evolutionary selection.

A search of Genbank with the genomic sequence of hedg-7 revealed a 94.7% identical sequence over 339 bp of the 3' flanking region of the genomic hedg-7 to the Genbank entry HSRTLIPE (accession X65642). The HSRTLIPE sequence was identified as a repetitive dinucleotide element within a cosmid clone (26710) from chromosome 19p13.1–19p13.2, containing a portion of the gene for hormone-sensitive lipase LIPE (Levitt et al, Cytogenet Cell Genet 1995;69:211–4). In view of the identity of HSRTLIPE and the hedg7 3'-flanking region, together with their virtually indistinguishable chromosomal localizations, we expect that the genes for hedg7 and the LIPE gene must be closely linked.

Nucleotide sequences encoding hedg-7 may be used to produce a purified oligo- or polypeptide using well known methods of recombinant DNA technology. Goeddel (1990, Gene Expression Technology, Methods and Enzymology, Vol. 185, Academic Press, San Diego Calif.) is one among many publications which teach expression of an isolated nucleotide sequence. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Cells transformed with DNA encoding HEDG-7 may be cultured under conditions suitable for the expression of T7Gs, their extracellular, transmembrane or intracellular domains and recovery of such peptides from cell culture. HEDG-7 (or any of its domains) produced by a recombinant cell may be secreted, expressend on cellular membranes or may be contained intracellularly, depending on the particular genetic construction used. In general, it is more convenient to prepare recombinant proteins in secreted form. Purification steps vary with the production process and the particular protein produced. Often an oligopeptide can be produced from a chimeric nucleotide sequence. This is accomplished by ligating the nucleotides from hedg-7 or a desired portion of the polypeptide to a nucleic acid sequence encoding a polypeptide domain which will facilitate protein purification (Kroll D J et al (1993) DNA Cell Biol. 12:441–53).

In addition to recombinant production, fragments of HEDG-7 may be produced by direct peptide synthesis using solid-phase techniques (e.g. Stewart at al (1969) Solid-Phase Peptide Synthesis, W H Freeman Co., San Francisco QA; Merrifield J (1963) J Am Chem. Soc. 85:2149–2154). Automated synthesis may be achieved, for example, using Applied Biosystems 431A Peptide Synthesizer (Foster City, Calif.) in accordance with the instructions provided by the manufacturer. Additionally, a particular portion of HEDG-7 may be mutated during direct synthesis and combined with other parts of the peptide using chemical methods.

HEDG-7 for antibody induction does not require biological activity: however, the protein must be antigenic. Peptides used to induce specific antibodies may have an aa sequence consisting of at least five amino acids (aa), preferably at least 10 aa. They should mimic a portion of the aa sequence of the protein and may contain the entire aa sequence of a small naturally occurring molecule such as HEDG-7. An antigenic portion of HEDG-7 may be fused to another protein such as keyhole limpet hemocyanin, and the chimeric molecule used for antibody production.

Antibodies specific for HEDG-7 may be produced by inoculation of an appropriate animal with the polypeptide or an antigenic fragment. An antibody is specific for HEDG-7 if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (e.g. Orlandi R et al (1989) PNAS 86:3833–3837, or Huse W D et al (1989) Science 256:1275–1281) or the in vitro stimulation of lymphocyte populations. Current technology (Winter G and Mistein C (1991) Nature 349:293–299) provides for a number of highly specific binding reagents based on the principles of antibody formation. These techniques may be adapted to produce molecules which specifically bind HEDG-7s.

The intracellular carboxy-terminal domain is usually involved in interactions with intracellular proteins, including those that transduce intracellular signals upon receptor activation. The HEDG-7 intracellular domain is located at amino acids 305–384 as set out in FIG. 2A. Furthermore, the carboxy-terminal domain is usually hydrophilic and highly antigenic relative to the receptor polypeptide as a whole. In addition, this domain normally shows greatly reduced conservation compared with other domains, and hence comprises a polypeptide sequence that is most unique to a given T7G receptor. Due to this diversity, this domain has special importance in the development of specific antibodies that can be used in diagnosis of HEDG-7 related diseases, identification of HEDG-7 expressing cell populations within a tissue or cell type, or for purification and isolation of polypeptides containing this sequence. Since multiple epitopes are recognized by polyclonal antibodies, a polypeptide of this length may contain several distinct epitopes, or epitopes only created by close proximity of non-adjacent peptide sequences due to folding a tertiary structure of the polypeptide.

An additional embodiment of the subject invention is the use of HEDG-7 specific antibodies, inhibitors, ligands or their analogs as bioactive agents to treat inflammation or disease including, but not limited to viral, bacterial or fungal infections; allergic responses; mechanical injury associated with trauma; hereditary diseases; lymphoma or carcinoma; or other conditions which activate the genes of kidney, lung, heart, lymphoid or tissues of the nervous system.

Bioactive compositions comprising agonists, antagonists, receptors or inhibitors of HEDG-7 may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving aberrant expression of the EDG-7 gene.

The examples below are provided to illustrate the subject invention. These examples are provided by way of illustration and are not included for the purpose of limiting the invention.

EXAMPLES

Example 1

Amplification of Partial Mouse edg-7 DNA by Polymerase Chain Reaction (PCR)

The Genbank database was surveyed for expressed sequence tags (EST's) representing novel G protein-coupled receptors (GPCRs) related to edg-1. This was done by searching the EST subset of Genbank via the Internet using the TBLASTN algorithm. This tool allows a given amino acid sequence (in this case the human edg-1 polypeptide) to be compared to each partial cDNA in the EST database, first translated into all 6 possible reading frames. The sequences showing the most relatedness to the edg-1 polypeptide were then classified as representing known (90% identical or more) or unknown (<90% identical) genes.

This analysis revealed 1 EST (Genbank accession number AA451451, derived from mouse mammary gland cDNA), which appeared to represent a new edg-related gene. This gene is referred to herein as mouse edg-7 or medg. This EST was used to further search the EST database for overlapping EST's derived from the same gene. This search revealed 1 additional EST (Genbank accession number AA254425, derived from mouse lymph node), which shared 100% identity over a 104 bp overlap. These 2 EST's was aligned and used to build an extended mouse edg-7 sequence. The partial translation product (213 aa) of this sequence showed 45.0% identity and 51.7% similarity to human edg-3, 42.8% identity and 54.6% similarity to human edg-1, and 32.9% identity and 42.8% similarity to rat edg-2. Thus, edg-7 appears to reside within the edg family of GPCRs, perhaps within the edg-1 subfamily (together with edg-3 and edg-4) rather than the edg-2 subfamily (with edg-5 and edg-6).

The assembled mouse partial edg-7 sequence was used to design oligonucleotide primers for PCR amplification. Since the normal tissue distribution of edg-7 was unknown, genomic DNA was used as the template for PCR. If introns interrupt the coding sequence of edg-7, such a PCR reaction might not be expected to work. However, our analysis of the highly-related genes edg-1 and edg-3 showed that no introns occur within the open reading frame. This differs from the slightly more distant edg-2 grouping of edg genes, in which 1 or more introns interrupt the open reading frame.

Mouse genomic DNA was amplified using the Expand™ PCR kit from Boehringer-Mannheim (Cat. 1681-842) in the following reaction:

| | |
|---|---|
| 6 μl | 10X PCR Buffer 1 (Expand ™ kit) |
| 8.4 μl | 2.5 mM mixture of each dNTP |
| 1.8 μl | 10 μM medg7-F2 primer: [5'-TATGTGCTCTTTTGTGTGGTGGTC-3'] |
| 1.8 μl | 10 μM medg7-R1 primer: [5'-AAGGTTCTTGTGTCCTGTCCCTTC-3'] |
| 0.9 μl | Expand ™ polymerase enzyme (3 units) |
| 40.1 μl | water |
| 1 μl | mouse genomic DNA (Promega; Cat. G309A) |

PCR conditions:

| | |
|---|---|
| Incubate: | 94° C. for 2 min |
| 30 cycles: | 92° C. for 1 min |

```
             -continued
             55° C. for 2 min

68° C. for 1 min

Incubate:    68° C. for 8 min

Hold:        4° C.
```

The amplified 600 bp DNA fragment (designated as sample no. 806-33) was purified using QIAquick PCR purification kit from Qiagen (Cat. 28106) and directly sequenced with an ABI 377 automated sequencer in-house, using the PCR primers to prime the sequencing reactions, and fluorescent dideoxy-terminator nucleotides to determine the sequence as per the manufacturer's suggested protocol.

Example 2

Isolation of Human Genomic DNA Clones Containing the edg-7 Gene

We made use of a commercially available human genomic DNA library, arrayed at high density on filter membranes, and probed these by hybridization with the radiolabeled partial mouse edg-7 cDNA of Example 1. Each arrayed clone contains a genomic DNA insert of about 120 kb in the BAC (bacterial artificial chromosome) plasmidic vector.

1. Screening of a human genomic DNA library consisting of high-density arrayed BAC clones with a radiolabeled degenerate oligonucleotide:

A degenerate edg-7 oligonucleotide Edg7-1 [5'-CTGCTCYASCMTSCTGCCCCTCTACTCCAAG-3'] was used to screen filters containing the high density arrayed BAC library (Genome Systems Inc.; Cat. BAC-5231) by hybridization under the following conditions: Hybridize at 50° C. overnight in:
   5× SSPE (2× SSPE is 0.36 M NaCl, 20 mM $NaH_2PO_4$, pH 7.4, 20 mM EDTA, pH 7.4)
   5× Denhardt's solution (1% Ficoll, 1% polyvinylpyrrolidone, 1% BSA)
   25 µg/ml herring sperm DNA
Wash 2 times for 30 min each at room temperature in:
   2× SSPE
   1% SDS
Wash 2 times for 20 min each at 50° C. in:
   2× SSPE
   1% SDS
Wash 2 times for 20 min each at 50° C. in:
   1× SSPE
   0.5% SDS
After rescreening these clones with radiolabeled partial mouse edg-7 PCR probe (sample 806-33, described above) one positive clone, 460D20 (identified by GSI as control no. 18241), was identified.

2. Screening of a human genomic DNA library consisting of high-density arrayed PAC clones with a radiolabeled partial mouse DNA (sample 806-33):

Random-primed, radiolabeled mouse edg-7 DNA sample 806-33 was used to screen filters containing the high density arrayed PAC library (Genome Systems Inc.; Cat. PAC-6541) by hybridization under the following conditions: Hybridize at 60° C. overnight in:
   5× SSPE (2× SSPE is 0.36 M NaCl, 20 mM $NaH_2PO_4$, pH 7.4, 20 mM EDTA, pH 7.4)
   5× Denhardt's solution (1% Ficoll, 1% polyvinylpyrrolidone, 1% BSA)
   25 µg/ml herring sperm DNA Wash 2 times for 30 min each at room temperature in:
   2× SSPE
   0.1% SDS
Wash 2 times for 20 min each at 50° C. in:
   2× SSPE
   0.1% SDS
Wash 2 times for 20 min each at 50° C. in:
   0.2× SSPE
   0.1% SDS One positive PAC clone, 230F18 (identified by GSI as control no. 19520) was identified and ordered from Genome Systems Inc. Rescreening of this clone with radiolabeled probe verified that the clone ordered was the one that gave the positive signal on hybridization screening.

Example 3

Subcloning of Full-length Human edg-7 DNA.

Southern blot analysis of the BAC and PAC clones using radiolabeled mouse edg-7 DNA sample 806-33 revealed the following hybridizing restriction fragments: HinDIII: >10 kb; EcoRI: >10 kn; MscI: 1.5 kb; DdeI: 0.7 kb. Each BAC or PAC clone was shotgun-subcloned into pBluescript II (SK+) (Stratagene; Cat. 212205) and the resulting colonies were screened by hybridization to radiolabeled mouse edg-7 DNA 806-33.

Clones containing the 1.5 kb MscI and 0.7 kb DdeI DNA fragments were sequenced. Sequence analysis confirmed that these clones contained portions of the human edg-7 gene. Based on the partial human edg-7 sequence, new primers were synthesized and more human edg-7 sequence was obtained from pBluescript clones containing the >10 kb HinDIII and EcoRI fragments. Additional sequencing primers were designed, and in this fashion the complete coding sequence of human edg-7 was determined. Furthermore, like other edg-1 subfamily members, no introns were found within the coding region of the edg-7 gene.

Two new primers were designed to facilitate the subcloning of an edg-7 DNA fragment encoding a full-length expressible edg-7 polypeptide into a eukaryotic expression vector. These were used to amplify human genomic DNA in a PCR reaction carried out under the following conditions:

```
4   µl      10X PCR Buffer 3

(Expand ™ kit)

0.8 µl      2.5 mM mixture of each dNTP 1.2 µl      10 µM H7-F14 primer:

[5'-GGAGGCCATGAACGCCACGGGGAC-3']

1.2 µl      10 µM H7-R19 primer:

[5'-AACTTCAGATGCTCCGCACGCTGGAG-3']

0.6 µl      Expand ™ polymerase enzyme (2 units)

31.2 µl     water

1   µl      human genomic DNA (Progmega;

Cat. G304A)
```

-continued

PCR conditions:

| | |
|---|---|
| Incubate : | 94° C. for 2 min |
| 30 cycles: | 94° C. for 1 min |
| | 60° C. for 30 sec |
| | 68° C. for 1.5 min |
| Incubate: | 68° C. for 8 min |
| Hold: | 4° C. |

The amplified 1.25 kb DNA fragment (designated as sample no. 1123-6) was purified using QIAquick PCR purification kit. This DNA was next re-amplified with edg-7 primers modified to contain restriction sites for convenient sub-cloning into the eukaryotic expression vector pcDNA3 (Invitrogen; discontinued), under the following conditions:

| | |
|---|---|
| 10 µl | 10X PCR Buffer 3 (Expand ™ kit) |
| 2.0 µl | 2.5 mM mixture of each dNTP |
| 3.0 µl | 10 µM H7-F24: [5'-TTTAAAAAGCTTGGAGGCCATGAACGCACGGGGAC-3'] |
| 3.0 µl | 10 µM H7-R21: [5'-TATATATCTAGAACTTCAGATGCTCCGCACGCTGGAG-3'] |
| 1.5 µl | Expand ™ polymerase enzyme (5 units) |
| 79.5 µl | water |
| 1 µl | human edg-7 PCR DNA sample 1123-6 |

PCR conditions:

| | |
|---|---|
| Incubate: | 94° C. for 2 min |
| 30 cycles: | 92° C. for 1 min |
| | 55° C. for 30 sec |
| | 68° C. for 1.5 min |
| Incubate: | 68° C. for 8 min |
| Hold: | 4° C. |

The amplified DNA fragment (designated as sample no. 1125-4) was purified, restricted with HinDIII and XbaI, then cloned into the appropriately prepared pcDNA3 vector. A clone, pC3-hEdg7, containing the edg-7 insert was isolated and a large-scale plasmid preparation was prepared for DNA sequencing and for transfection and subsequent expression analysis in eukaryotic cells. FIG. 1A illustrates the nucleotide sequence for hedg-7 derived the Bac and Pac clones. FIG. 2A illustrates the TM regions and the predicted amino acid sequence. FIG. 3A is an alignment of the nucleotide sequence with the amino acid sequence.

Example 4

Isolation of BAC Clones Containing the Mouse edg-7 Gene

The partial mouse edg-7 DNA sample 806-33 was used to screen filters containing high-density arrayed mouse genomic DNA BAC clones from Genome Systems Inc. (Cat. BAC-4921) by filter hybridization. The following conditions were employed:

Hybridize at 64° C. overnight in:
 5× SSPE
 5× Denhardt's solution
 25 µg/ml herring sperm DNA
Wash 2 times for 30 min each at room temperature in:
 2× SSPE
 0.1% SDS
Wash 2 times for 20 min each at 50° C. in:
 2× SSPE
 0.1% SDS
Wash 2 times for 20 min each at 50° C. in:
 0.2× SSPE
 0.1% SDS Three positive clones were identified from this screen: 76N3 (GSI control no. 19983), 61L2 (control no. 19984) and 61013 (control no. 19985). PCR amplification of the three clones with primers medg7-F2 and medg7-R1 (for details see Example 1) produced a 600 bp PCR product in each case, indicating that all 3 clones contain mouse edg-7 sequence. Considering the size of the inserts, it is reasonable to assume that at least 1 of the 3 clones may contain the complete mouse edg-7 gene.

Example 5

Cloning of Partial Rat edg-7 cDNA Sequence

A. PCR Amplification of a Rat edg-7 cDNA Fragment.

The primers medg7-F2 and medg7-R1 were used to amplify a rat hypothalamus cDNA library (RHT) prepared in-house. This library was synthesized from random-primed first strand cDNA and cloned unidirectionally into the HinDIII/NotI sites of the pcDNA3 expression vector. PCR was performed under the following conditions:

| | |
|---|---|
| 2 µl | 10X PCR Buffer 1 (Expand ™ kit) |
| 2.8 µl | 2.5 mM mixture of each dNTP |
| 0.6 µl | 10 µM medg7-F2 primer |
| 0.6 µl | 10 µM medg7-R1 primer |

| | |
|---|---|
| 0.3 µl | Expand ™ polymerase enzyme (1 unit) |
| 12.7 µl | water |
| 1 µl | RHT cDNA complete library miniprep DNA |
| | PCR conditions: |
| Incubate: | 92° C. for 2 min |
| 30 cycles: | 92° C. for 40 sec |
| | 52° C. for 1 min |
| | 68° C. for 1 min |
| Incubate: | 68° C. for 8 min |
| Hold: | 4° C. |

A 600 bp product was seen, demonstrating that the RHT cDNA library contained clone(s) representing the rat edg-7 gene.

B. Screening 2777-clone Pools of RHT cDNA Library for edg-7 clones.

A series of pools containing a calculated 2777 clones per pool were screened using the medg7-F2 and medg7-R1 primers under the conditions specified in A above. Out of 884 pools screened, only 1 pool was positive for the 600 bp PCR product of the edg-7 PCR. This pool (no. 198) was used for further study.

C. Amplification of Rat edg-7 cDNA from RHT Pool 198.

By using 1 specific primer (medg7-F2 or medg7-R1) vs one vector-based primer, the cDNA insert from RHT pool 198 was amplified in 2 overlapping pieces. Since the cDNA inserts were directionally cloned, the appropriate combination of specific vs vector primer could easily be chosen. Reaction conditions are shown below:

```
Vector-based primers:

830F:       [5'-TAGAGAACCCACTGCTTAC-3']

1186R:      [5'-CCCAGAATAGAATGACACC-3']

2 µl     10X PCR Buffer 1 (Expand ™ kit)

2.8 µl     2.5 mM mixture of each dNTP 0.6 µl     10 µM mouse edg-7 specific primer 0.6 µl     10 µM vector primer 0.3 µl     Expand ™ polymerase enzyme (2 units)

12.7 µl     water

1 µl     RHT pool 198 miniprep DNA

PCR conditions:

Incubate:    92° C. for 2 min 30 cycles:   92° C. for 40 sec

50° C. for 1 min

68° C. for 3 min

Incubate:    68° C. for 8 min

Hold:         4° C.
```

The most prominent bands (800 bp from primer set 830F vs medg7-R1 and 1.3 kb from primer set medg7-F2 vs 1186R) were reamplified, purified and sequenced. The nucleotide sequence is presented in FIG. 5 and the amino acid sequence is in FIG. 6.

Example 6

Cloning and Expression of HEDG7 from Human Jurkat T-cell cDNA

To determine the agonist specificity and demonstrate methods for using HEDG7 in drug discovery, it was desirable to isolate a full-length cDNA clone from a human source. For this purpose, numerous cDNA libraries and first strand cDNA pools, were surveyed by PCR to identify sources for further analysis. From this survey, a commercially available cDNA library (Origene Technologies, Cat. DLH-115) prepared from the human Jurkat T-cell lymphoma cell line was chosen. The previously described PCR primers H7-F14 and H7-R19 were used as follows to amplify any full-length cDNA that might be found in this cDNA library:

All PCR amplifications were carried out with the Expand™ PCR kit (Boehringer-Mannheim, Cat. 1681-842). The reaction contained the following reagents:

| | |
|---|---|
| 2 µl | 10x PCR Buffer 3 |
| 0.4 µl | 25 mM dNTP mix |
| 0.6 µl | Primer H7-F14 (10 pmol/µl) |
| 0.6 µl | Primer H7-R19 (10 pmol/µl) |
| 0.3 µl | Expand polymerase (3 units) |
| 15.1 µl | water |
| 1 µl | cDNA from Origene library DLH-115 |
| | (as supplied by manufacturer) |
| | PCR conditions: |
| Incubate: | 94° C. for 2 min |
| 30 cycles: | 94° C. for 1 min |
| | 60° C. for 1 min |
| | 68° C. for 2 min |
| Incubate: | 68° C. for 8 min |
| Hold: | 4° C. |

The PCR reaction (tracking number 80629-50) amplified a 1200 bp DNA fragment. This was used as template to re-amplify human edg7 with primers H7-F23 and H7-R21, described previously, containing restriction sites for subcloning into the eukaryotic expression vector pcDNA3.1 (Invitrogen, Cat V790-20).

Each reaction contained the following reagents:

| | |
|---|---|
| 5 µl | 10x PCR Buffer 3 |
| 1.0 µl | 25 mM dNTP mix |
| 1.5 µl | Primer H7-F23 (10 pm/µl) |
| 1.5 µl | Primer H7-R21 (10 pm/µl) |
| 0.75 µl | Expand ™ polymerase (5 units) |
| 39.25 µl | water |
| 1 µl | 80629-50 DNA |
| | PCR conditions: |
| Incubate: | 94° C. for 2 min |
| 10 cycles: | 94° C. for 1 min |
| | 55° C. for 1 min |
| | 68° C. for 2 min |
| 15 cycles: | 94° C. for 1 min |
| | 68° C. for 3 min |
| Incubate: | 68° C. for 8 min |
| Hold: | 4° C. |

The amplified fragments from PCR reactions 80630-21 and 80630-22 were purified using QIAquick PCR purification kit (Qiagen, Cat.28106), pooled and designated as insert hedg7-M. The hedg7-M cDNA was restricted with Hind III and Xba I, purified using the QIAquick PCR purification kit, then isolated after agarose gel electrophoresis and purified with the QIAquick Gel Extraction kit (Qiagen, Cat. 28704).

The cDNA fragment was then subcloned into HindIII and XbaI restricted pcDNA3.1 (Invitrogen).

Miniprep DNA from 4 clones was tested by cotransfection into 293-EBNA cells (Invitrogen, Cat. R620-07) with a 2× SRE-Luciferase reporter gene constructed in-house. We previously determined that these cells are an ideal expression host for edg receptors that respond to sphingolipids, since only a single edg gene is expressed (the LPA receptor subtype edg-5, see U.S. Ser. No. 08/997,803), under normal culture conditions. All other cell types tested showed a complex edg receptor expression pattern, together with unacceptable responsiveness to S1P, SPC, LPA, or more than one of these lysolipids. Thus, the low endogenous expression of previously identified S1P receptor subtypes (edg-1, edg-3, edg-4/H218) and hedg7 (determined here) permits overexpression and functional analysis of these receptors in a relatively unresponsive cell background. From this preliminary cotransfection experiment, the expression clone pC3-hEdg7#M10 was chosen for further analysis. The nucleotide sequence and amino acid sequence of the hedg-7 sequence from the pC3-hEdg7#M10 clone are shown in FIG. 1B and FIG. 2B, respectively. Furthermore, an alignment of the hedg-7 amino acid sequence from the pC3-hEdg7#M10 clone and from the genomic DNA sequence is shown in FIG. 3B.

The EBNA-293 cells when transfected with DNAs of clone pc3-hedg7#M10 and 2× SRE-Luciferase reporter gave a 5.3- and 6.5-fold response to 10 μM S1P treatment in 2 independent experiments. (FIG. 7)

Transient transfection protocol for 293-EBNA:

Day 1.

1) 100 mm plates of 293-EBNA with a confluency of ~80% were used for transfection.
2) SRE Reporter Gene Cotransfection: Expression plasmid (3.5 g) and reporter plasmid (2× SREtk-p4Luc-zeo; 0.5 μg) DNA samples were combined and diluted in 750 μl of DMEM/F12 (serum-free media) and 20 μl Plus Reagent (Lipofectamine Plus Kit, Life Technologies Cat. 10964-013), and incubated at room temperature for 15 min.
3) 30 μl Lipofectamine Reagent (Lipofectamine Plus Kit) was diluted in 750 μl DMEM/F12. The diluted Lipofectamine was then combined with the DNA/Plus mixture and incubated at RT for 15 min.
4) The 293-EBNA plates were washed once with PBS, and 5 ml DMEM/F12 was added to each plate.
5) DNA/Plus/Lipofectamine mixture was added to each plate of 293-EBNA cells. The plates were left for 3 hr at 37° C. in a 5% $CO_2$ incubator.
6) The transfection medium was replaced with DMEM/F12 containing 10% FBS to recover overnight.

Day 2.

2) Transfected cells were harvested by trypsinization and 20,000 cells per well were plated in 96-well Blackview plates coated with poly D-lysine (Becton Dickinson Labware, Cat. 40640). Medium was DMEM/F12 plus 0.15% FBS. No. cells were plated in the outside wells of the 96-well plate. Cells were returned to the incubator for 48 hr.

Day 4.

1) Media was removed and cells treated with compounds diluted in serum-free DMEM/F12 media and the following treatments: a) Untreated: Serum-free DMEM/F12; b) 10 μM S1P in DMEM/F12 medium.
2) The cells were treated 5 hr in the 37° C. incubator.
3) Luclite kit (Packard; Cat. 6016911) was used for luciferase assay. All reagents were brought to room temperature before use.
4) Media was removed from each well. 50 μl 0.5M HEPES pH 7.8, 1 mM $MgCl_2$, 1 mM $CaCl_2$ was added to all wells of 96-well plate.
5) Luclite substrate was made up and 50 μl substrate was added to each well as specified in the kit.
6) Plates were incubated at room temperature for 30 min.
7) After incubation, plates were counted in a 12-detector Packard Top Count on a program without dark delay.

Example 7

Agonist Specificity of HEDG7

To determine the agonist specificity of HEDG-7, 293-EBNA cells were transfected with pc3-hedg7#M10, serum-deprived as described above, and treated in serum-free medium with 5 μM concentrations of SPC, S1P, LPA, lysophosphatiylcholine (LPC), edelfosine, psychosine, anandamide or 2-arachidonylglycerol. Control cells were treated with serum-free medium alone, and the SRE response was expressed as fold induction relative to this control. After 5 hr of treatment, luciferase activity was measured.

Results: Both SPC and S1P robustly induced expression of the SRE reporter gene in cells transfected with pc3-hedg7#M10 (FIG. 8). In contrast, LPA, LPC and edelfosine failed to activate the SRE response, supporting the assignment of edg-7 as a S1P receptor subtype, along with edg-1, edg-3 and edg-4/H218. This finding is also in accord with the lack of coding region introns found in these 4 receptor genes.

Example 8

Determination of Relative Potency and Efficacy of HEDG7 Receptor Agonists

One aspect of the present invention is a method for using recombinant HEDG7 receptors in drug screening programs. Although the use of T7G receptors in high-throughput screening is well-known, no such screen has been reported for the HEDG-7 receptor. More specifically, the novel HEDG7 receptor presented herein can be used to identify and rank the relative potency and efficacy of potential agonists. These compounds may be useful inasmuch as they would be expected to modulate cellular or physiological responses to HEDG7 agonists, or to initiate or supplement HEDG7 signaling in cells where the receptor occurs. Equally, once a quantitative and reliable assay is established, it can readily be applied to identify and rank the relative potency and efficacy of receptor antagonists.

Transfection of a HEDG7 expression vector pc3-hedg7#M10 was carried out using Lipofectamine Plus (Life Technologies, Cat. 10964-013) according to manufacturer's instructions. The next day, transfected cells were harvested by trypsinization and replated at 30,000 cells per well in poly-(D)lysine-coated 96-well plates in medium containing 0.15% FBS. The next day, cells were treated in serum-free medium containing different concentrations of various sphingolipids. To demonstrate the utility of HEDG7 in drug discovery, we tested the ligand specificity and responsiveness of HEDG7 in a similar manner.

Various concentrations of S1P, SPC, psychosine, glucopsychosine or dihydrosphingosine 1-phosphate (dihydro-S1P) were applied in triplicate to cells in 96-well plates, and luciferase levels were measured after 6 hr treatment. Results were tabulated in Microsoft Excel, and analyzed with GraphPad Prism software. $EC_{50}$ values were determined using a fixed Hill-slope equation, unless variable slope significantly improved the fit to the data. The luciferase response was expressed as fold response, after subtracting any endogenous response in pcDNA3-transfected cells at a given concentration of compound. The experiment was repeated three times with similar results, and a representative experiment is shown in FIG. 9.

Results: Table 1 summarizes the relative potency and efficacy of the compounds tested. The concentration-dependent response to these sphingolipids is shown in FIG. 9.

TABLE 1

Potency and relative efficacy of sphingolipids in 293-EBNA cells transfected with pc3-hedg7#M10.

| Compound | $EC_{50}$ (M) | Rank | Max. Fold | $E_{Max}$ (Percent) | Rank |
| --- | --- | --- | --- | --- | --- |
| S1P | 1.87 | 1 | 3.59 | 100 | 1 |
| SPC | 3.95 | 2 | 3.59 | 100 | 1 |
| Psychosine | N.A. | — | 1.00 | 0 | — |
| Glucopsychosine | N.A. | — | 1.00 | 0 | — |

N.A. Since no response was seen at nontoxic concentrations, $EC_{50}$ and rank could not be determined.

From the results obtained here, it can be concluded that HEDG7 responds to both S1P and SPC as full agonists, though S1P showed a lower $EC_{50}$ than SPC. In contrast, psychosine and glucopsychosine both failed to activate HEDG7 at nontoxic concentrations. Published literature supports the existence of multiple receptors for S1P, the identity of at least some of these with SPC receptors, subtype-selective differences in the relative potencies of S1P and SPC, and the possible existence of receptor(s) for psychosine and glucopsychosine. Here we have demonstrated that HEDG7 is a receptor for S1P and SPC, but not psychosine or glucopsychosine. With a method for screening, S1P receptor subtypes and ranking relative potency and efficacy of analogs and/or organic heterocycles, there is little doubt that rapid improvements can be made on the medicinal chemistry of S1P. These novel compounds, in turn, can be used to treat hyper- or hypo-proliferative diseases, and modulate inflammatory and antigen-specific immune responses as described elsewhere in this document.

Example 9

Detection of hedg Polynucleotides by Hybridization with hedg

Hedg polynucleotides can vary through the introduction of natural or artificial mutations or through cloning and subsequent manipulations. Moreover, the mammalian homolog of a given gene usually varies by 10–30% from species to species, as a result of nucleotide changes that have accumulated through their divergent evolutionary history. Therefore, a method is provided herein for the detection and identification of hedg variants and other highly related genes.

The HEDG7 coding region of hedg is prepared by restriction of either pC3-hEdg7 or pc3-hedg7#M10 with HinDIII and XbaI, followed by cDNA insert purification using standard techniques after agarose gel electrophoresis. The cDNA insert may be labeled using $^{32}$P-nucleotide end-labeling or random priming (several kits are commercially available), or through incorporation of non-natural nucleotides for later detection with antibodies by methods well known in the art. Nylon filters (e.g. Hybond N+, Cat. RPN132B) bearing a polynucleotide or mixture of polynucleotides are prepared by standard techniques. Examples include Southern blots, filter lifts from bacterial colonies or bacteriophage plaques and the like.

The dried filters are rehydrated in water, then prehybridized in a sealable bag with 10 ml (or enough to cover filters and seal the bag) of hybridization solution (48% deionized formamide, 4.8× SSC [20× SSC is 3 M NaCl, 0.3 M sodium citrate, pH 7.0], 1× Denhardt's solution [50× Denhardt's is 1% Ficoll 400, 1% polyvinylpyrrolidone, 1% BSA (Pentax Fraction V)], 10% dextran sulfate, 0.1% sodium dodecyl sulfate [SDS]) for 1 hr or more at 42° C.

Radiolabeled probe is added to 1 ml of sonicated herring sperm DNA (2 mg/ml) in a screw-cap tube and incubated in a boiling water bath for 10 min. Transfer the tube to ice, add 2 ml of hybridization solution and inject the probe solution into the sealed bag. Sufficient probe should be added to give 1 to 15 ng of radiolabeled probe/ml hybridization buffer (final volume) at >5×10$^7$ cpm/g DNA. Reseal the bag, mix thoroughly and incubate overnight at 42° C. in a shaking or rotating water bath or incubator.

Wash filters three times with 500 ml of low-stringency wash buffer (2× SSC, 0.1 SDS) at RT for 15 min per wash, on a slowly rotating platform. Then wash two times with medium-stringency wash buffer (1× SSC, 0.1% SDS) at 65° C. 15 min per wash. Dry the filters and expose to Phosphorimager cassette or autoradiography film. Positive spots or DNA bands are identified after subtraction of background or appropriate negative control samples (see below).

If needed, a DNA spot containing 10 pmol of the full-length hedg insert of pC3-hEdg7 can be used as a positive control (Pos) on the filter, and a DNA spot containing 10 pmol of full-length human edg-1 insert (edg-1 open reading frame only) can be used as a negative control (Neg). The full-length open reading frame of a test DNA (also 10 pmol) will be scored as a positive if the integrated optical density (IOD) of the radioactive probe hybridizing to the test DNA (Test) is greater than $IOD_{Neg}+(IOD_{Pos}-IOD_{Neg})/2$. Otherwise, the test DNA will be scored as negative. A positive test correlates with approximately at least 70% identitiy, and more preferably at least 80–85 sequence identity. If a partial-length open reading frame of the test gene is used, then the equivalent regions of edg-7 and edg-1 will be used as positive and negative controls, respectively, for hybridization.

Example 10

Antisense Analysis

Knowledge of the correct, complete cDNA sequence of HEDG-7 enables its use as a tool for antisense technology in the investigation of gene function. Oligonucleotides, cDNA or genomic fragments comprising the antisense strand of hedg-7 are used either in vitro or in vivo to inhibit expression of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression is obtained by designing antisense sequences to intron regions, promoter/enhancer elements, or even to trans-acting regulatory genes. Similarly, inhibition is achieved using Hogeboom base-pairing methodology, also known as "triple helix" base pairing.

Example 11

Expression of HEDG-7

Expression of hedg-7 is accomplished by subcloning the cDNAs into appropriate expression vectors and transfecting the vectors into analogous expression hosts for example *E. Coli*. In a particular case, the vector is engineered such that it contains a promoter for β-galactosidase, upstream of the cloning site, followed by sequence containing the amino-terminal Met and the subsequent 7 residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with IPTG using standard methods produces a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it is obtained by deletion or insertion of the appropriate number of bases using well known methods including in vitro mutagenesis, digestion with exonuclease III or mung bean nuclease, or the inclusion of an oligonucleotide linker of appropriate length.

The hedg-7 cDNA is shuttled into other vectors known to be useful for expression of protein in specific hosts. Oligonucleotide primers containing cloning sites as well as a segment of DNA (about 25 bases) sufficient to hybridize to stretches at both ends of the target cDNA is synthesized chemically by standard methods. These primers are then used to amplify the desired gene segment by PCR. The resulting gene segment is digested with appropriate restriction enzymes under standard conditions and isolated by gel electrophoresis. Alternately, similar gene segments are produced by digestion of the cDNA with appropriate restriction enzymes. Using appropriate primers, segments of coding sequence from more than one gene are ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector also includes an origin of replication to allow propagation in bacteria and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, are used in mammalian host cells. Once homogeneous cultures of recombinant cells are obtained through standard culture methods, large quantities of recombinantly produced HEDG-7 are recovered from the conditioned medium and analyzed using chromatographic methods known in the art. For example, HEDG-7 can be expressibly cloned into the expression vector pcDNA3, as exemplified herein. This product can be used to transform, for example, HEK293 or COS by methodology standard in the art. Specifically, for example, using Lipofectamine (Gibco BRL catalog no. 18324-020) mediated gene transfer.

Example 12

Isolation of Recombinant HEDG-7

HEDG-7 is expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen) between the purification domain and the HEDG-7 sequence is useful to facilitate expression of HEDG-7.

Example 13

Testing of Chimeric T7Gs

Functional chimeric T7Gs are constructed by combining the extracellular and/or transmembrane ligand-receptive sequences of a new isoform with the transmembrane and/or intracellular segments of a different T7G for test purposes. This concept was demonstrated by Kobilka et al (1988, Science 240:1310–1316) who created a series of chimeric α2-β2 adrenergic receptors (AR) by inserting progressively greater amounts of α2-AR transmembrane sequence into β2-AR. The binding activity of known agonists changed as the molecule shifted from having more α2 than β2 conformation, and intermediate constructs demonstrated mixed specificity. The specificity for binding antagonists, however, correlated with the source of the domain VII. The importance of T7G domain VII for ligand recognition was also found in chimeras utilizing two yeast α-factor receptors and is significant because the yeast receptors are classified as miscellaneous receptors. Thus, functional role of specific domains appears to be preserved throughout the T7G family regardless of category.

In parallel fashion, internal segments or cytoplasmic domains from a particular isoform are exchanged with the analogous domains of a known T7G and used to identify the structural determinants responsible for coupling the receptors to trimeric G-proteins (Dohlman et al (1991) Annu Rev Biochem 60:653–88). A chimeric receptor in which domains V, VI, and the intracellular connecting loop from β2-AR were substituted into a2-AR was shown to bind ligands with a2-AR specificity, but to stimulate adenylate cyclase in the manner of β2-AR. This demonstrates that for adrenergic-type receptors, G-protein recognition is present in domains V and VI and their connecting loop. The opposite situation was predicted and observed for a chimera in which the V→VI loop from α1-AR replaced the corresponding domain on β2-AR and the resulting receptor bound ligands with β2-AR specificity and activated G-protein-mediated phosphatidylinositol turnover in the α1-AR manner. Finally, chimeras constructed from muscarinic receptors also demonstrated that V→VI loop is the major determinant for specificity of G-protein activity (Bolander FF, supra).

Chimeric or modified T7Gs containing substitutions in the extracellular and transmembrane regions have shown that these portions of the receptor determine ligand binding specificity. For example, two Ser residues conserved in domain V of all adrenergic and D catecholamine T7G receptors are necessary for potent agonist activity. These serines are believed to form hydrogen bonds with the catechol moiety of the agonists within the T7G binding site. Similarly, an Asp residue present in domain III of all T7Gs which bind biogenic amines is believed to form an ion pair with the ligand amine group in the T7G binding site.

Functional, cloned T7Gs are expressed in heterologous expression systems and their biological activity assessed (e.g. Marullo et al (1988) Proc Natl Acad Sci 85:7551–55; King et al (1990) Science 250:121–23). One heterologous system introduces genes for a mammalian T7G and a mammalian G-protein into yeast cells. The T7G is shown to have appropriate ligand specificity and affinity and trigger appropriate biological activation—growth arrest and morphological changes—of the yeast cells.

An alternate procedure for testing chimeric receptors is based on the procedure utilizing the $P_{2u}$ purinergic receptor ($P_{2u}$) as published by Erb et al (1993, Proc Natl Acad Sci 90:104411–53). Function is easily tested in cultured K562 human leukemia cells because these cells lack $P_{2u}$ receptors. K562 cells are transfected with expression vectors containing either normal or chimeric $P_{2u}$ and loaded with fura-a, fluorescent probe for Ca++. Activation of properly assembled and functional $P_{2u}$ receptors with extracellular UTP or ATP mobilizes intracellular Ca++ which reacts with fura-a and is measured spectrofluorometrically. As with the T7G receptors above, chimeric genes are created by combining sequences for extracellular receptive segments of any newly discovered T7G polypeptide with the nucleotides for the transmembrane and intracellular segments of the known $P_2U$ molecule. Bathing the transfected K562 cells in microwells containing appropriate ligands triggers binding and fluorescent activity defining effectors of the T7G molecule. Once ligand and function are established, the $P_{2u}$ system is useful for defining antagonists or inhibitors which block binding and prevent such fluorescent reactions.

Example 14

Production of HEDG-7 Specific Antibodies

Two approaches are utilized to raise antibodies to HEDG-7, and each approach is useful for generating either polyclonal or monoclonal antibodies. In one approach, denatured protein from reverse phase HPLC separation is obtained in quantities up to 75 mg. This denatured protein is used to immunize mice or rabbits using standard protocols; about 100 micrograms are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg is sufficient for labeling and screening of several thousand clones.

In the second approach, the amino acid sequence of an appropriate HEDG-7 domain, as deduced from translation of the cDNA, is analyzed to determine regions of high antigenicity. Oligopeptides comprising appropriate hydrophilic regions, as illustrated in FIG. 2A, are synthesized and used in suitable immunization protocols to raise antibodies. Analysis to select appropriate epitopes is described by Ausubel F M et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St. Louis Mo.) by reaction with M-maleimidobenzoyl-N-hydroxysuccinimide ester (MBS; Ausubel F M et al, supra). If necessary, a cysteine is introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine sewm albumin, reacting with antisera, washing and reacting with labeled (radioactive or fluorescent), affinity purified, specific goat anti-rabbit 1 gG.

Hybridomas are prepared and screened using standard techniques. Hybridomas of interest are detected by screening with labeled HEDG-7 to identify those fusions producing the monoclonal antibody with the desired specificity. In a typical protocol, wells of plates (FAST; Becton-Dickinson, Palo Alto Calif.) are coated during incubation with affinity purified, specific rabbit anti-mouse (or suitable antispecies 1 g) antibodies at 10 mg/ml. The coated wells are blocked with 1% BSA, washed and incubated with supematants from hybridomas. After washing the wells are incubated with labeled HEDG-7 at 1 mg/ml. Supernatants with specific antibodies bind more labeled HEDG-7 than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascetic fluid by affinity chromatography on Protein A. Monoclonal antibodies with affinities of at least $10^8$ M$^{-1}$, preferably $10^9$ to $10^{10}$ or stronger, are typically made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

Example 15

Diagnostic Test Using HEDG-7 Specific Antibodies

Particular HEDG-7 antibodies are useful for investigating signal transduction and the diagnosis of infectious or hereditary conditions which are characterized by differences in the amount or distribution of HEDG-7 or downstream products of an active signaling cascade.

Diagnostic tests for HEDG-7 include methods utilizing antibody and a label to detect HEDG-7 in human body fluids, membranes, cells, tissues or extracts of such. The polypeptides and antibodies of the present invention are used with or without modification. Frequently, the polypeptides and antibodies are labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, Incorporated herein by reference.

A variety of protocols for measuring soluble or membrane-bound HEDG-7, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on HEDG-7 is preferred, but a competitive binding assay may be employed. These assays are described, among other places, in Maddox, D E et al (1983, J Exp. Med. 158:1211f).

Example 16

Purification of Native HEDG-7 Using Specific Antibodies

Native or recombinant HEDG-7 is purified by immunoaffinity chromatography using antibodies specific for HEDG-7. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of HEDG-7 by preparing a fraction from cells containing HEDG-7 in a soluble form. This preparation is derived by solubilization of whole cells or of a subcellular fraction obtained via differential centrifugation (with or without addition of detergent) or by other methods well known in the art. Alternatively, soluble HEDG-7 containing a signal sequence is secreted in useful quantity into the medium in which the cells are grown.

A soluble HEDG-7-containing preparation is passed over the immunoaffinity column, and the column is washed under conditions that allow the preferential absorbance of HEDG-7 (e.g., high ionic strength buffers in the presence of detergent). Then, the column is eluted under conditions that disrupt antibody/protein binding (e.g., a buffer of pH 2–3 or a high concentration of a chaotrope such as urea or thiocyanate ion), and HEDG-7 is collected.

Example 17

Drug Screening

This invention is particularly useful for screening therapeutic compounds by using HEDG-7 or binding fragments thereof in any of a variety of drug screening techniques. As HEDG-7 is a G protein coupled receptor any of the methods commonly used in the art may potentially used to identify HEDG-7 ligands. For example, the activity of a G protein coupled receptor such as HEDG-7 can be measured using any of a variety of appropriate functional assays in which activation of the receptor results in an observable change in the level of some second messenger system, such as adenylate cyclase, guanylyl cyclase, calcium mobilization, or inositol phospholipid hydrolysis. One such approach, measures the effect of ligand binding on the activation of intracellular second messenger pathways, using a reporter gene. Typically, the reporter gene will have a promoter which is sensitive to the level of that second messenger controlling expression of an easily detectable gene product, for example, CAT or luciferase. Alternatively, the cell is loaded with a reporter substance, e.g., FURA, which detects alterations in the intracellular level of calcium, can be used to monitor modulation of the receptor as a result of ligand binding. Thus, the present invention provides methods of screening for drugs or any other agents which affect signal transduction.

Alternatively, the polypeptide or fragment employed in such a test is either free in solution, affixed to a solid support, borne on a cell surface or located intracellularly. One method of drug screening utilizes eukaryotic or prokaryotic host cells (or membrane preparations therefrom) which are stably transformed with recombinant nucleic acids expressing the polypeptide or fragment. Drugs are screened against such transformed cells in competition binding assays. Such cells, either in viable or fixed form, are used for standard binding assays. $^{32}$P-labelled S1P could be used in such a competition binding assay for HEDG-7. One measures, for example, the formation of complexes between HEDG-7 and the agent being tested. Alternatively, one examines the diminution in complex formation between HEDG-7 and a ligand (for example, S1P), caused by the agent being tested.

Example 18

Rational Drug Design

Herein, the goal of rational drug design is to produce structural analogs of biologically active phospholipids of interest or of small molecules with which they interact, agonists, antagonists, or inhibitors. Any of these examples are used to fashion drugs which are more active or stable forms of the phospholipid or which enhance or interfere with the function of a phospholipid in vivo.

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design includes molecules which have improved activity or stability as shown by Braxton S and Wells J A (1992, Biochemistry 31:7796–7801) or which act as inhibitors, agonists, or antagonists of native peptides as shown by Athauda S B et al (1993 J Biochem 113:742–46), incorporated herein by reference.

Example 19

Use and Administration of Antibodies, Inhibitors, or Antagonists

Antibodies, inhibitors, or antagonists of HEDG-7 (or other treatments to limit signal transduction, LST) provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, half-life and antigenicity/immunogenicity. These and other characteristics aid in defining an effective carrier.

LSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger HEDG-7 activity are treatable with LSTs. These conditions or diseases are specifically diagnosed by the tests discussed above, and such testing should be performed in suspected cases of viral, bacterial or fungal infections: allergic responses; mechanical injury associated with trauma; hereditary diseases; lymphoma or carcinoma; or other conditions which activate the genes of lymphoid or neuronal tissues.

Example 20

Production of Transgenic Animals

Animal model systems which elucidate the physiological and behavioral roles of the HEDG-7 receptor are produced by creating transgenic animals in which the activity of the HEDG-7 receptor is either increased or decreased, or the amino acid sequence of the expressed HEDG-7 receptor is altered, by a variety of techniques. Examples of these techniques include, but are not limited to: 1) Insertion of normal or mutant versions of DNA encoding a HEDG-7 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these HEDG-7 receptor sequences. The technique of homologous recombination is well known in the art. It replaces the native gene with the inserted gene and so is useful for producing an animal that cannot express native HEDG-7 receptors but does express, for example, an inserted mutant HEDG-7 receptor, which has replaced the native HEDG-7 receptor in the animal's genome by recombination, resulting in underexpression of the transporter. Microinjection adds genes to the genome, but does not remove them, and so is useful for producing an animal which expresses its own and added HEDG-7 receptors, resulting in overexpression of the HEDG-7 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a HEDG-7 purified from a vector by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only methods for inserting DNA into the egg cell, and is used here only for exemplary purposes.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments.

SEQUENCE LISTING

<160> NUMBER OF SEQ ID NOS: 21

<210> SEQ ID NO 1
<211> LENGTH: 24
<212> TYPE: DNA
<213> ORGANISM: Artificial Sequence

```
<220> FEATURE:
<223> OTHER INFORMATION: Description of Artificial Sequence: synthetic
      primer

<400> SEQUENCE: 1
tatgtgctct tttgtgtggt ggtc                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 2
aaggttcttg tgtcctgtcc cttc                                              24

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: synthetic
      primer

<400> SEQUENCE: 3
ctgctcyasc mtsctgcccc tctactccaa g                                      31

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 4
ggaggccatg aacgccacgg ggac                                              24

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 5
aacttcagat gctccgcacg ctggag                                            26

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 6
tttaaaaagc ttggaggcca tgaacgcacg gggac                                  35

<210> SEQ ID NO 7
<211> LENGTH: 37
<212> TYPE: DNA
<213> ORGANISM: Artificial Sequence
<220> FEATURE:
```

```
<223> OTHER INFORMATION: Description of Artificial Sequence: synthetic
      primer

<400> SEQUENCE: 7
tatatatcta gaacttcaga tgctccgcac gctggag                                37

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 8
tagagaaccc actgcttac                                                   19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 9
cccagaatag aatgacacc                                                   19

<210> SEQ ID NO 10
<211> LENGTH: 2270
<212> TYPE: DNA
<213> ORGANISM: Homo sapiens
<220> FEATURE:
<221> NAME/KEY: CDS
<222> LOCATION: (16)..(1170)

<400> SEQUENCE: 10
cccccggggg aggcc atg aac gcc acg ggg acc ccg gtg gcc ccc gag tcc         51
                 Met Asn Ala Thr Gly Thr Pro Val Ala Pro Glu Ser
                  1               5                  10 tgc caa cag ctg gcg gcc ggc ggg cac agc cgg ctc att gtt ctg cac          99
Cys Gln Gln Leu Ala Ala Gly Gly His Ser Arg Leu Ile Val Leu His
         15                  20                  25 tac aac cac tcg ggc cgg ctg gcc ggg cgc ggg ggg ccg gag gat ggc         147
Tyr Asn His Ser Gly Arg Leu Ala Gly Arg Gly Gly Pro Glu Asp Gly
     30                  35                  40 ggc ctg ggg gcc ctg cgg ggg ctg tcg gtg gcc gcc agc tgc ctg gtg         195
Gly Leu Gly Ala Leu Arg Gly Leu Ser Val Ala Ala Ser Cys Leu Val
 45                  50                  55                  60 gtg ctg gag aac ttg ctg gtg ctg gcg gcc atc acc agc cac atg cgg         243
Val Leu Glu Asn Leu Leu Val Leu Ala Ala Ile Thr Ser His Met Arg
                 65                  70                  75 tcg cga cgc tgg gtc tac tat tgc ctg gtg aac atc acg ctg agt gac         291
Ser Arg Arg Trp Val Tyr Tyr Cys Leu Val Asn Ile Thr Leu Ser Asp
             80                  85                  90 ctg ctc acg ggc gcg gcc tac ctg gcc aac gtg ctg ctg tcg ggg gcc         339
Leu Leu Thr Gly Ala Ala Tyr Leu Ala Asn Val Leu Leu Ser Gly Ala
         95                 100                 105 cgc acc ttc cgt ctg gcg ccc gcc cag tgg ttc cta cgg gag ggc ctg         387
Arg Thr Phe Arg Leu Ala Pro Ala Gln Trp Phe Leu Arg Glu Gly Leu
    110                 115                 120 ctc ttc acc gcc ctg gcc gcc tcc acc ttc agc ctg ctc ttc act gca         435
Leu Phe Thr Ala Leu Ala Ala Ser Thr Phe Ser Leu Leu Phe Thr Ala
125                 130                 135                 140
```

```
ggg gag cgc ttt gcc acc atg gtg cgg ccg gtg gcc gag agc ggg gcc    483
Gly Glu Arg Phe Ala Thr Met Val Arg Pro Val Ala Glu Ser Gly Ala
            145                 150                 155 acc aag acc agc cgc gtc tac ggc ttc atc ggc ctc tgc tgg ctg ctg    531
Thr Lys Thr Ser Arg Val Tyr Gly Phe Ile Gly Leu Cys Trp Leu Leu
        160                 165                 170 gcc gcg ctg ctg ggg atg ctg cct ttg ctg ggc tgg aac tgc ctg tgc    579
Ala Ala Leu Leu Gly Met Leu Pro Leu Leu Gly Trp Asn Cys Leu Cys
                175                 180                 185 gcc ttt gac cgc tgc tcc agc ctt ctg ccc ctc tac tcc aag cgc tac    627
Ala Phe Asp Arg Cys Ser Ser Leu Leu Pro Leu Tyr Ser Lys Arg Tyr
            190                 195                 200 atc ctc ttc tgc ctg gtg atc ttc gcc ggc gtc ctg gcc acc atc atg    675
Ile Leu Phe Cys Leu Val Ile Phe Ala Gly Val Leu Ala Thr Ile Met
205                 210                 215                 220 ggc ctc tat ggg gcc atc ttc cgc ctg gtg cag gcc agc ggg cag aag    723
Gly Leu Tyr Gly Ala Ile Phe Arg Leu Val Gln Ala Ser Gly Gln Lys
                225                 230                 235 gcc cca cgc cca gcg gcc cgc cgc aag gcc cgc cgc ctg ctg aag acg    771
Ala Pro Arg Pro Ala Ala Arg Arg Lys Ala Arg Arg Leu Leu Lys Thr
            240                 245                 250 gtg ctg atg atc ctg ctg gcc ttc ctg gtg tgc tgg ggc cca ctc ttc    819
Val Leu Met Ile Leu Leu Ala Phe Leu Val Cys Trp Gly Pro Leu Phe
        255                 260                 265 ggg ctg ctg ctg gcc gac gtc ttt ggc tcc aac ctc tgg gcc cag gag    867
Gly Leu Leu Leu Ala Asp Val Phe Gly Ser Asn Leu Trp Ala Gln Glu
        270                 275                 280 tac ctg cgg ggc atg gac tgg atc ctg gcc ctg gcc gtc ctc aac tcg    915
Tyr Leu Arg Gly Met Asp Trp Ile Leu Ala Leu Ala Val Leu Asn Ser
285                 290                 295                 300 gcg gtc aac ccc atc atc tac tcc ttc cgc agc agg gag gtg tgc aga    963
Ala Val Asn Pro Ile Ile Tyr Ser Phe Arg Ser Arg Glu Val Cys Arg
                305                 310                 315 gcc gtg ctc agc ttc ctc tgc tgc ggg tgt ctc cgg ctg ggc atg cga    1011
Ala Val Leu Ser Phe Leu Cys Cys Gly Cys Leu Arg Leu Gly Met Arg
            320                 325                 330 ggg ccc ggg gac tgc ctg gcc cgg gcc gtc gag gct cac tcc gga gct    1059
Gly Pro Gly Asp Cys Leu Ala Arg Ala Val Glu Ala His Ser Gly Ala
        335                 340                 345 tcc acc acc gac agc tct ctg agg cca agg gac agc ttt cgc ggc tcc    1107
Ser Thr Thr Asp Ser Ser Leu Arg Pro Arg Asp Ser Phe Arg Gly Ser
        350                 355                 360 cgc tcg ctc agc ttt cgg atg cgg gag ccc ctg tcc agc atc tcc agc    1155
Arg Ser Leu Ser Phe Arg Met Arg Glu Pro Leu Ser Ser Ile Ser Ser
365                 370                 375                 380 gtg cgg agc atc tga agttgcagtc ttgcgtgtgg atggtgcagc caccgggtgc    1210
Val Arg Ser Ile gtgccaggca ggccctcctg gggtacagga agctgtgtgc acgcagcctc gcctgtatgg    1270
ggagcaggga acgggacagg cccccatggt cttcccggtg gcctctcggg gcttctgacg    1330
ccaaatgggc ttcccatggt caccctggac aaggaggcaa ccaccccacc tccccgtagg    1390
agcagagagc accctggtgt gggggcgagt gggttcccca caacccccgct ctctgtgtgat    1450 tctgggaag tcccggcccc tctctgggcc tcagtagggc tcccaggctg caaggggtgg    1510
actgtgggat gcatgccctg gcaacattga agttcgatca tggtacgtga tgttgcggcc    1570
tcttattccc tggtgcgtgc atgtgtgggg gccgtggctc agggggctg tggatctagg    1630 ggcagccggg tgtgtctttg ctagagaggg ccacgggcca gtgccctgtg agggtggaga    1690
```

```
gtgtgtgtgt gtgtgtgtgt gtgtgtgtgg acaacytctg ggcgttgcgg gaagtggggg      1750
tgacaatgac agttaatgcc gctcttcttg ttcacttccc ctttagaaat ggcagggccc      1810
atgccccatc tctggcytct gcatcttttg gggacccact ctctgggct ggcagaggca       1870 ccaccttggc ttcctgggct gggggaatct tccctcacat ccccttcagc atgaacggcc      1930
tcggctttcc cggtgggtaa aacagtttaa tcactgaagc cgaagcacag ggttgatggt      1990
acacgctccc cgccagccac agggctgac gactgcctgc cccgtgaaac tccagtggag       2050
acgtttcagc tccacaccat tcagtatggg agacgccagc cccacgggc tacggtgcaa       2110 gcagataact gaatttcgaa gtgtaggttg tgtttaattt gaatctgttt atatttcggt      2170
agccccatgg ggcgggtggg ggggatccac tagttctaga gcggccgcca ccgcggtgga      2230
gctccagywt twgwtccckt tagtgagggt taattgcgcg                            2270
```

<210> SEQ ID NO 11
<211> LENGTH: 384
<212> TYPE: PRT
<213> ORGANISM: Homo sapiens

<400> SEQUENCE: 11

```
Met Asn Ala Thr Gly Thr Pro Val Ala Pro Glu Ser Cys Gln Gln Leu
  1               5                  10                  15

Ala Ala Gly Gly His Ser Arg Leu Ile Val Leu His Tyr Asn His Ser
             20                  25                  30

Gly Arg Leu Ala Gly Arg Gly Pro Glu Asp Gly Leu Gly Ala
         35                  40                  45

Leu Arg Gly Leu Ser Val Ala Ala Ser Cys Leu Val Leu Glu Asn
     50                  55                  60

Leu Leu Val Leu Ala Ala Ile Thr Ser His Met Arg Ser Arg Arg Trp
 65                  70                  75                  80

Val Tyr Tyr Cys Leu Val Asn Ile Thr Leu Ser Asp Leu Leu Thr Gly
                 85                  90                  95

Ala Ala Tyr Leu Ala Asn Val Leu Leu Ser Gly Ala Arg Thr Phe Arg
            100                 105                 110

Leu Ala Pro Ala Gln Trp Phe Leu Arg Glu Gly Leu Leu Phe Thr Ala
        115                 120                 125

Leu Ala Ala Ser Thr Phe Ser Leu Leu Phe Thr Ala Gly Glu Arg Phe
    130                 135                 140

Ala Thr Met Val Arg Pro Val Ala Glu Ser Gly Ala Thr Lys Thr Ser
145                 150                 155                 160

Arg Val Tyr Gly Phe Ile Gly Leu Cys Trp Leu Leu Ala Ala Leu Leu
                165                 170                 175

Gly Met Leu Pro Leu Leu Gly Trp Asn Cys Leu Cys Ala Phe Asp Arg
            180                 185                 190

Cys Ser Ser Leu Leu Pro Leu Tyr Ser Lys Arg Tyr Ile Leu Phe Cys
        195                 200                 205

Leu Val Ile Phe Ala Gly Val Leu Ala Thr Ile Met Gly Leu Tyr Gly
    210                 215                 220

Ala Ile Phe Arg Leu Val Gln Ala Ser Gly Gln Lys Ala Pro Arg Pro
225                 230                 235                 240

Ala Ala Arg Arg Lys Ala Arg Arg Leu Leu Lys Thr Val Leu Met Ile
                245                 250                 255

Leu Leu Ala Phe Leu Val Cys Trp Gly Pro Leu Phe Gly Leu Leu Leu
            260                 265                 270
```

-continued

```
Ala Asp Val Phe Gly Ser Asn Leu Trp Ala Gln Glu Tyr Leu Arg Gly
            275                 280                 285

Met Asp Trp Ile Leu Ala Leu Ala Val Leu Asn Ser Ala Val Asn Pro
        290                 295                 300

Ile Ile Tyr Ser Phe Arg Ser Arg Glu Val Cys Arg Ala Val Leu Ser
305                 310                 315                 320

Phe Leu Cys Cys Gly Cys Leu Arg Leu Gly Met Arg Gly Pro Gly Asp
                325                 330                 335

Cys Leu Ala Arg Ala Val Glu Ala His Ser Gly Ala Ser Thr Thr Asp
            340                 345                 350

Ser Ser Leu Arg Pro Arg Asp Ser Phe Arg Gly Ser Arg Ser Leu Ser
        355                 360                 365

Phe Arg Met Arg Glu Pro Leu Ser Ser Ile Ser Ser Val Arg Ser Ile
370                 375                 380
```

<210> SEQ ID NO 12
<211> LENGTH: 1176
<212> TYPE: DNA
<213> ORGANISM: Homo sapiens
<220> FEATURE:
<221> NAME/KEY: CDS
<222> LOCATION: (13)..(1167)

<400> SEQUENCE: 12

```
aagcttgcca cc atg aac gcc acg ggg acc ccg gtg gcc ccc gag tcc tgc      51
              Met Asn Ala Thr Gly Thr Pro Val Ala Pro Glu Ser Cys
                1               5                  10 caa cag ctg gcg gcc ggc ggg cac agc cgg ctc att gtt ctc cac tac        99
Gln Gln Leu Ala Ala Gly Gly His Ser Arg Leu Ile Val Leu His Tyr
 15                  20                  25 aac cac tcg ggc cgg ctg gcc ggg cgc ggg ggg ccg gag gat ggc ggc       147
Asn His Ser Gly Arg Leu Ala Gly Arg Gly Gly Pro Glu Asp Gly Gly
 30                  35                  40                  45 ctg ggg gcc ctg cgg ggg ctg tcg gtg gcc gcc agc tgc ctg gtg gtg       195
Leu Gly Ala Leu Arg Gly Leu Ser Val Ala Ala Ser Cys Leu Val Val
                 50                  55                  60 ctg gag aac ttg ctg gtg ctg gcg gcc atc acc agc cac atg cgg tcg       243
Leu Glu Asn Leu Leu Val Leu Ala Ala Ile Thr Ser His Met Arg Ser
             65                  70                  75 cga cgc tgg gtc tac tat tgc ctg gtg aac atc acg ctg agt gac ctg       291
Arg Arg Trp Val Tyr Tyr Cys Leu Val Asn Ile Thr Leu Ser Asp Leu
         80                  85                  90 ctc acg ggc gcg gcc tac ctg gcc aac gtg ctg ctg tcg ggg gcc cgc       339
Leu Thr Gly Ala Ala Tyr Leu Ala Asn Val Leu Leu Ser Gly Ala Arg
     95                  100                 105 acc ttc cgt ctg gcg ccc gcc cag tgg ttc cta cgg gag ggc ctg ctc       387
Thr Phe Arg Leu Ala Pro Ala Gln Trp Phe Leu Arg Glu Gly Leu Leu
110                 115                 120                 125 ttc acc gcc ctg gcc gcc tcc acc ttc agc ctg ctc ttc act gta ggg       435
Phe Thr Ala Leu Ala Ala Ser Thr Phe Ser Leu Leu Phe Thr Val Gly
                130                 135                 140 gag cgc ttt gcc acc atg gtg cgg ccg gtg gcc gag agc ggg gcc acc       483
Glu Arg Phe Ala Thr Met Val Arg Pro Val Ala Glu Ser Gly Ala Thr
            145                 150                 155 aag acc agc cgc gtc tac ggc ttc atc ggc ctc tgc tgg ctg ctg gcc       531
Lys Thr Ser Arg Val Tyr Gly Phe Ile Gly Leu Cys Trp Leu Leu Ala
        160                 165                 170 gcg ctg ctg ggg atg ctg cct ttg ctg ggc tgg aac tgc ctg tgc gcc       579
Ala Leu Leu Gly Met Leu Pro Leu Leu Gly Trp Asn Cys Leu Cys Ala
```

```
              175                 180                 185
ttt gac cgc tgc tcc agc ctt ctg ccc ctc tac tcc aag cgc tac atc      627
Phe Asp Arg Cys Ser Ser Leu Leu Pro Leu Tyr Ser Lys Arg Tyr Ile
190                 195                 200                 205 ctc ttc tgc ctg gtg atc ttc gcc ggc gtc ctg gcc acc atc atg ggc      675
Leu Phe Cys Leu Val Ile Phe Ala Gly Val Leu Ala Thr Ile Met Gly
                210                 215                 220 ctc tat ggg gcc atc ttc cgc ctg gtg cag gcc agc ggg cag aag gcc      723
Leu Tyr Gly Ala Ile Phe Arg Leu Val Gln Ala Ser Gly Gln Lys Ala
                225                 230                 235 cca cgc cca gcg gcc cgc cgc aag gcc cgc cgc ctg ctg aag acg gtg      771
Pro Arg Pro Ala Ala Arg Arg Lys Ala Arg Arg Leu Leu Lys Thr Val
                240                 245                 250 ctg atg atc ctg ctg gcc ttc ctg gtg tgc tgg ggc cca ctc ttc ggg      819
Leu Met Ile Leu Leu Ala Phe Leu Val Cys Trp Gly Pro Leu Phe Gly
255                 260                 265 ctg ctg ctg gcc gac gtc ttt ggc tcc aac ctc tgg gcc cag gag tac      867
Leu Leu Leu Ala Asp Val Phe Gly Ser Asn Leu Trp Ala Gln Glu Tyr
270                 275                 280                 285 ctg cgg ggc atg gac tgg atc ctg gcc ctg gcc gtc ctc aac tcg gcg      915
Leu Arg Gly Met Asp Trp Ile Leu Ala Leu Ala Val Leu Asn Ser Ala
                290                 295                 300 gtc aac ccc atc atc tac tcc ttc cgc agc agg gag gtg tgc aga gcc      963
Val Asn Pro Ile Ile Tyr Ser Phe Arg Ser Arg Glu Val Cys Arg Ala
                305                 310                 315 gtg ctc agc ttc ctc tgc tgc ggg tgt ctc cgg ctg ggc atg cga ggg     1011
Val Leu Ser Phe Leu Cys Cys Gly Cys Leu Arg Leu Gly Met Arg Gly
                320                 325                 330 ccc ggg gac tgc ctg gcc cgg gcc gtc gag gct cac tcc gga gct tcc     1059
Pro Gly Asp Cys Leu Ala Arg Ala Val Glu Ala His Ser Gly Ala Ser
335                 340                 345 acc acc gac agc tct ctg agg cca agg gac agc ttt cgc ggc tcc cgc     1107
Thr Thr Asp Ser Ser Leu Arg Pro Arg Asp Ser Phe Arg Gly Ser Arg
350                 355                 360                 365 tcg ctc agc ttt cgg atg cgg gag ccc ctg tcc agc agc tcc agc gtg     1155
Ser Leu Ser Phe Arg Met Arg Glu Pro Leu Ser Ser Ser Ser Ser Val
                370                 375                 380 cgg agc atc tga agttctaga                                            1176
Arg Ser Ile <210> SEQ ID NO 13
<211> LENGTH: 384
<212> TYPE: PRT
<213> ORGANISM: Homo sapiens

<400> SEQUENCE: 13

Met Asn Ala Thr Gly Thr Pro Val Ala Pro Glu Ser Cys Gln Gln Leu
1               5                   10                  15

Ala Ala Gly Gly His Ser Arg Leu Ile Val Leu His Tyr Asn His Ser
                20                  25                  30

Gly Arg Leu Ala Gly Arg Gly Gly Pro Glu Asp Gly Gly Leu Gly Ala
            35                  40                  45

Leu Arg Gly Leu Ser Val Ala Ala Ser Cys Leu Val Val Leu Glu Asn
        50                  55                  60

Leu Leu Val Leu Ala Ala Ile Thr Ser His Met Arg Ser Arg Arg Trp
65                  70                  75                  80

Val Tyr Tyr Cys Leu Val Asn Ile Thr Leu Ser Asp Leu Leu Thr Gly
                85                  90                  95
```

```
Ala Ala Tyr Leu Ala Asn Val Leu Leu Ser Gly Ala Arg Thr Phe Arg
            100                 105                 110
Leu Ala Pro Ala Gln Trp Phe Leu Arg Glu Gly Leu Leu Phe Thr Ala
            115                 120                 125
Leu Ala Ala Ser Thr Phe Ser Leu Leu Phe Thr Val Gly Glu Arg Phe
            130                 135                 140
Ala Thr Met Val Arg Pro Val Ala Glu Ser Gly Ala Thr Lys Thr Ser
145                 150                 155                 160
Arg Val Tyr Gly Phe Ile Gly Leu Cys Trp Leu Leu Ala Ala Leu Leu
                165                 170                 175
Gly Met Leu Pro Leu Leu Gly Trp Asn Cys Leu Cys Ala Phe Asp Arg
            180                 185                 190
Cys Ser Ser Leu Leu Pro Leu Tyr Ser Lys Arg Tyr Ile Leu Phe Cys
            195                 200                 205
Leu Val Ile Phe Ala Gly Val Leu Ala Thr Ile Met Gly Leu Tyr Gly
            210                 215                 220
Ala Ile Phe Arg Leu Val Gln Ala Ser Gly Gln Lys Ala Pro Arg Pro
225                 230                 235                 240
Ala Ala Arg Arg Lys Ala Arg Arg Leu Leu Lys Thr Val Leu Met Ile
                245                 250                 255
Leu Leu Ala Phe Leu Val Cys Trp Gly Pro Leu Phe Gly Leu Leu Leu
            260                 265                 270
Ala Asp Val Phe Gly Ser Asn Leu Trp Ala Gln Glu Tyr Leu Arg Gly
            275                 280                 285
Met Asp Trp Ile Leu Ala Leu Ala Val Leu Asn Ser Ala Val Asn Pro
            290                 295                 300
Ile Ile Tyr Ser Phe Arg Ser Arg Glu Val Cys Arg Ala Val Leu Ser
305                 310                 315                 320
Phe Leu Cys Cys Gly Cys Leu Arg Leu Gly Met Arg Gly Pro Gly Asp
                325                 330                 335
Cys Leu Ala Arg Ala Val Glu Ala His Ser Gly Ala Ser Thr Thr Asp
            340                 345                 350
Ser Ser Leu Arg Pro Arg Asp Ser Phe Arg Gly Ser Arg Ser Leu Ser
            355                 360                 365
Phe Arg Met Arg Glu Pro Leu Ser Ser Ser Ser Val Arg Ser Ile
            370                 375                 380

<210> SEQ ID NO 14
<211> LENGTH: 1152
<212> TYPE: DNA
<213> ORGANISM: Homo sapiens

<400> SEQUENCE: 14
atgaacgcca cggggacccc ggtggccccc gagtcctgcc aacagctggc ggccggcggg      60
cacagccggc tcattgttct gcactacaac cactcgggcc ggctggccgg gcgcggggg     120
ccggaggatg gcggcctggg ggccctgcgg gggctgtcgg tggccgccag ctgcctggtg     180
gtgctggaga acttgctggt gctggcggcc atcaccagcc acatgcggtc gcgacgctgg     240
gtctactatt gcctggtgaa catcacgctg agtgacctgc tcacgggcgc ggcctacctg     300
gccaacgtgc tgctgtcggg ggcccgcacc ttccgtctgg cgcccgccca gtggttccta     360
cgggagggcc tgctcttcac cgccctggcc gcctccacct tcagcctgct cttcactgta     420
ggggagcgct ttgccaccat ggtgcggccg gtggccgaga gcggggccac caagaccagc     480
cgcgtctacg gcttcatcgg cctctgctgg ctgctggccg cgctgctggg gatgctgcct     540
```

-continued

```
ttgctgggct ggaactgcct gtgcgccttt gaccgctgct ccagccttct gcccctctac    600
tccaagcgct acatcctctt ctgcctggtg atcttcgccg cgtcctggc caccatcatg    660 ggcctctatg ggccatcttc ccgcctggtg caggccagcg ggcagaaggc cccacgccca    720
gcggcccgcc gcaaggcccg ccgcctgctg aagacggtgc tgatgatcct gctggccttc    780
ctggtgtgct ggggcccact cttcgggctg ctgctggcca cgtctttgg ctccaacctc    840 tgggcccagg agtacctgcg gggcatggac tggatcctgg ccctggccgt cctcaactcg    900
gcggtcaacc ccatcatcta ctccttccgc agcagggagg tgtgcagagc cgtgctcagc    960
ttcctctgct gcgggtgtct ccggctgggc atgcgagggc cggggactg cctggcccgg    1020 gccgtcgagg ctcactccgg agcttccacc accgacagct ctctgaggcc aagggacagc    1080
tttcgcggct cccgctcgct cagctttcgg atgcgggagc ccctgtccag cagctccagc    1140
gtgcggagca tc                                                       1152
```

<210> SEQ ID NO 15
<211> LENGTH: 364
<212> TYPE: PRT
<213> ORGANISM: Unknown
<220> FEATURE:
<223> OTHER INFORMATION: Description of Unknown Organism: Mammalian EDG

<400> SEQUENCE: 15

```
Met Ala Ala Ile Ser Thr Ser Ile Pro Val Ile Ser Gln Pro Gln Phe
  1               5                  10                  15

Thr Ala Met Asn Glu Pro Gln Cys Phe Tyr Asn Glu Ser Ile Ala Phe
             20                  25                  30

Phe Tyr Asn Arg Ser Gly Lys His Leu Ala Thr Glu Trp Asn Thr Val
         35                  40                  45

Ser Lys Leu Val Met Gly Leu Gly Ile Thr Val Cys Ile Phe Ile Met
     50                  55                  60

Leu Ala Asn Leu Leu Val Met Val Ala Ile Tyr Val Asn Arg Arg Phe
 65                  70                  75                  80

His Phe Pro Ile Tyr Tyr Leu Met Ala Asn Leu Ala Ala Ala Asp Phe
                 85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
        115                 120                 125

Asp Thr Ser Leu Thr Ala Ser Val Ala Asn Leu Leu Ala Ile Ala Ile
    130                 135                 140

Glu Arg His Ile Thr Val Phe Arg Met Gln Leu His Thr Arg Met Ser
145                 150                 155                 160

Asn Arg Arg Val Val Val Val Ile Val Val Ile Trp Thr Met Ala Ile
                165                 170                 175

Val Met Gly Ala Ile Pro Ser Val Gly Trp Asn Cys Ile Cys Asp Ile
            180                 185                 190

Glu Asn Cys Ser Asn Met Ala Pro Leu Tyr Ser Asp Ser Tyr Leu Val
        195                 200                 205

Phe Trp Ala Ile Phe Asn Leu Val Thr Phe Val Val Met Val Val Leu
    210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
```

```
                    245                 250                 255
Leu Lys Thr Val Val Ile Val Leu Gly Ala Phe Ile Ile Cys Trp Thr
            260                 265                 270

Pro Gly Leu Val Leu Leu Leu Asp Val Cys Pro Gln Cys Asp
        275                 280                 285

Val Leu Ala Tyr Glu Lys Phe Phe Leu Leu Ala Glu Phe Asn Ser
        290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Ser Glu Asn Pro Thr Gly
                325                 330                 335

Pro Thr Glu Ser Ser Asp Arg Ser Ala Ser Ser Leu Asn His Thr Ile
            340                 345                 350

Leu Ala Gly Val His Ser Asn Asp His Ser Val Val
            355                 360

<210> SEQ ID NO 16
<211> LENGTH: 353
<212> TYPE: PRT
<213> ORGANISM: Unknown
<220> FEATURE:
<223> OTHER INFORMATION: Description of Unknown Organism: Mammalian EDG

<400> SEQUENCE: 16

Met Asn Glu Cys His Tyr Asp Lys His Met Asp Phe Phe Tyr Asn Arg
1               5                   10                  15

Ser Asn Thr Asp Thr Val Asp Asp Trp Thr Gly Thr Lys Leu Val Ile
            20                  25                  30

Val Leu Cys Val Gly Thr Phe Phe Cys Leu Phe Ile Phe Phe Ser Asn
        35                  40                  45

Ser Leu Val Ile Ala Ala Val Ile Lys Asn Arg Lys Phe His Phe Pro
    50                  55                  60

Phe Tyr Tyr Leu Leu Ala Asn Leu Ala Ala Ala Asp Phe Phe Ala Gly
65                  70                  75                  80

Ile Ala Tyr Val Phe Leu Met Phe Asn Thr Gly Pro Val Ser Lys Thr
                85                  90                  95

Leu Thr Val Asn Arg Trp Phe Leu Arg Gln Gly Leu Leu Asp Ser Ser
            100                 105                 110

Leu Thr Ala Ser Leu Thr Asn Leu Leu Val Ile Ala Val Glu Arg His
        115                 120                 125

Met Ser Ile Met Arg Met Arg Val His Ser Asn Leu Thr Lys Lys Arg
130                 135                 140

Val Thr Leu Leu Ile Leu Leu Val Trp Ala Ile Ala Ile Phe Met Gly
145                 150                 155                 160

Ala Val Pro Thr Leu Gly Trp Asn Cys Leu Cys Asn Ile Ser Ala Cys
                165                 170                 175

Ser Ser Leu Ala Pro Ile Tyr Ser Arg Ser Tyr Leu Val Phe Trp Thr
            180                 185                 190

Val Ser Asn Leu Met Ala Phe Leu Ile Met Val Val Val Tyr Leu Arg
        195                 200                 205

Ile Tyr Val Tyr Val Lys Arg Lys Thr Asn Val Leu Ser Pro His Thr
    210                 215                 220

Ser Gly Ser Ile Ser Arg Arg Arg Thr Pro Met Lys Leu Met Lys Thr
225                 230                 235                 240

Val Met Thr Val Leu Gly Ala Phe Val Val Cys Trp Thr Pro Gly Leu
```

```
                    245                 250                     255
Val Val Leu Leu Leu Asp Gly Leu Asn Cys Arg Gln Cys Gly Val Gln
            260                 265                 270

His Val Lys Arg Trp Phe Leu Leu Ala Leu Leu Asn Ser Val Val
            275                 280                 285

Asn Pro Ile Ile Tyr Ser Tyr Lys Asp Glu Asp Met Tyr Gly Thr Met
        290                 295                 300

Lys Lys Met Ile Cys Cys Phe Ser Gln Glu Asn Pro Glu Arg Arg Pro
305                 310                 315                 320

Ser Arg Ile Pro Ser Thr Val Leu Ser Arg Ser Asp Thr Gly Ser Gln
                325                 330                 335

Tyr Ile Glu Asp Ser Ile Ser Gln Gly Ala Val Cys Asn Lys Ser Thr
            340                 345                 350

Ser

<210> SEQ ID NO 17
<211> LENGTH: 381
<212> TYPE: PRT
<213> ORGANISM: Unknown
<220> FEATURE:
<223> OTHER INFORMATION: Description of Unknown Organism: Mammalian EDG

<400> SEQUENCE: 17

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
        35                  40                  45

Ser Val Val Phe Ile Leu Ile Cys Cys Phe Ile Ile Leu Glu Asn Ile
    50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Leu Ser Ile Val Ile Leu Tyr Cys Arg Ile
    210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Asn Val Ala Leu Leu Lys Thr
                245                 250                 255
```

```
Val Ile Ile Val Leu Ser Val Phe Ile Ala Cys Trp Ala Pro Leu Phe
                260                 265                 270

Ile Leu Leu Leu Leu Asp Val Gly Cys Lys Val Lys Thr Cys Asp Ile
            275                 280                 285

Leu Phe Arg Ala Glu Tyr Phe Leu Val Leu Ala Val Leu Asn Ser Gly
        290                 295                 300

Thr Asn Pro Ile Ile Tyr Thr Leu Thr Asn Lys Glu Met Arg Arg Ala
305                 310                 315                 320

Phe Ile Arg Ile Met Ser Cys Cys Lys Cys Pro Ser Gly Asp Ser Ala
                325                 330                 335

Gly Lys Phe Lys Arg Pro Ile Ile Ala Gly Met Glu Phe Ser Arg Ser
            340                 345                 350

Lys Ser Asp Asn Ser Ser His Pro Gln Lys Asp Glu Gly Asp Asn Pro
        355                 360                 365

Glu Thr Ile Met Ser Ser Gly Asn Val Asn Ser Ser Ser
    370                 375                 380

<210> SEQ ID NO 18
<211> LENGTH: 378
<212> TYPE: PRT
<213> ORGANISM: Unknown
<220> FEATURE:
<223> OTHER INFORMATION: Description of Unknown Organism: Mammalian EDG

<400> SEQUENCE: 18

Met Ala Thr Ala Leu Pro Pro Arg Leu Gln Pro Val Arg Gly Asn Glu
 1               5                  10                  15

Thr Leu Arg Glu His Tyr Gln Tyr Val Gly Lys Leu Ala Gly Arg Leu
                20                  25                  30

Lys Glu Ala Ser Glu Gly Ser Thr Leu Thr Thr Val Leu Phe Leu Val
            35                  40                  45

Ile Cys Ser Phe Ile Val Leu Glu Asn Leu Met Val Leu Ile Ala Ile
        50                  55                  60

Trp Lys Asn Asn Lys Phe His Asn Arg Met Tyr Phe Phe Ile Gly Asn
65                  70                  75                  80

Leu Ala Leu Cys Asp Leu Leu Ala Gly Ile Ala Tyr Lys Val Asn Ile
                85                  90                  95

Leu Met Ser Gly Lys Lys Thr Phe Ser Leu Ser Pro Thr Val Trp Phe
            100                 105                 110

Leu Arg Glu Gly Ser Met Phe Val Ala Leu Gly Ala Ser Thr Cys Ser
        115                 120                 125

Leu Leu Ala Ile Ala Ile Glu Arg His Leu Thr Met Ile Lys Met Arg
    130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
            180                 185                 190

Ser Lys Lys Tyr Ile Ala Phe Cys Ile Ser Ile Phe Thr Ala Ile Leu
        195                 200                 205

Val Thr Ile Val Ile Leu Tyr Ala Arg Ile Tyr Phe Leu Val Lys Ser
    210                 215                 220

Ser Ser Arg Lys Val Ala Asn His Asn Asn Ser Glu Arg Ser Met Ala
225                 230                 235                 240
```

-continued

```
Leu Leu Arg Thr Val Val Ile Val Val Ser Val Phe Ile Ala Cys Trp
                245                 250                 255
Ser Pro Leu Phe Ile Leu Phe Leu Ile Asp Val Ala Cys Arg Val Gln
            260                 265                 270
Ala Cys Pro Ile Leu Phe Lys Ala Gln Trp Phe Ile Val Leu Ala Val
            275                 280                 285
Leu Asn Ser Ala Met Asn Pro Val Ile Tyr Thr Leu Ala Ser Lys Glu
    290                 295                 300
Met Arg Arg Ala Phe Phe Arg Leu Val Cys Asn Cys Leu Val Arg Gly
305                 310                 315                 320
Arg Gly Ala Arg Ala Ser Pro Ile Gln Pro Ala Leu Asp Pro Ser Arg
                325                 330                 335
Ser Lys Ser Ser Ser Ser Asn Asn Ser Ser His Ser Pro Lys Val Lys
            340                 345                 350
Glu Asp Leu Pro His Thr Asp Pro Ser Ser Cys Ile Met Asp Lys Asn
            355                 360                 365
Ala Ala Leu Gln Asn Gly Ile Phe Cys Asn
    370                 375
```

<210> SEQ ID NO 19
<211> LENGTH: 353
<212> TYPE: PRT
<213> ORGANISM: Unknown
<220> FEATURE:
<223> OTHER INFORMATION: Description of Unknown Organism: Mammalian EDG

<400> SEQUENCE: 19

```
Met Gly Ser Leu Tyr Ser Glu Tyr Leu Asn Pro Asn Lys Val Gln Glu
1               5                   10                  15
His Tyr Asn Tyr Thr Lys Glu Thr Leu Glu Thr Gln Glu Thr Thr Ser
            20                  25                  30
Arg Gln Val Ala Ser Ala Phe Ile Val Ile Leu Cys Cys Ala Ile Val
            35                  40                  45
Val Glu Asn Leu Leu Val Leu Ile Ala Val Ala Arg Asn Ser Lys Phe
    50                  55                  60
His Ser Ala Met Tyr Leu Phe Leu Gly Asn Leu Ala Ala Ser Asp Leu
65                  70                  75                  80
Leu Ala Gly Val Ala Phe Val Ala Asn Thr Leu Leu Ser Gly Ser Val
                85                  90                  95
Thr Leu Arg Leu Thr Pro Val Gln Trp Phe Ala Arg Glu Gly Ser Ala
            100                 105                 110
Phe Ile Thr Leu Ser Ala Ser Val Phe Ser Leu Leu Ala Ile Ala Ile
            115                 120                 125
Glu Arg His Val Ala Ile Ala Lys Val Lys Leu Tyr Gly Ser Asp Lys
    130                 135                 140
Ser Cys Arg Met Leu Leu Leu Ile Gly Ala Ser Trp Leu Ile Ser Leu
145                 150                 155                 160
Val Leu Gly Gly Leu Pro Ile Leu Gly Trp Asn Cys Leu Gly His Leu
                165                 170                 175
Glu Ala Cys Ser Thr Val Leu Pro Leu Tyr Ala Lys His Tyr Val Leu
            180                 185                 190
Cys Val Val Thr Ile Phe Ser Ile Ile Leu Leu Ala Val Val Ala Leu
            195                 200                 205
Tyr Val Arg Ile Tyr Cys Val Val Arg Ser Ser His Ala Asp Met Ala
    210                 215                 220
```

-continued

```
Ala Pro Gln Thr Leu Ala Leu Leu Lys Thr Val Thr Ile Val Leu Gly
225                 230                 235                 240

Val Phe Ile Val Cys Trp Leu Pro Ala Phe Ser Ile Leu Leu Leu Asp
                245                 250                 255

Tyr Ala Cys Pro Val His Ser Cys Pro Ile Leu Tyr Lys Ala His Tyr
            260                 265                 270

Leu Phe Ala Val Ser Thr Leu Asn Ser Leu Leu Asn Pro Val Ile Tyr
        275                 280                 285

Thr Trp Arg Ser Arg Asp Leu Arg Arg Glu Val Leu Arg Pro Leu Gln
    290                 295                 300

Cys Trp Arg Pro Gly Val Gly Val Gln Gly Arg Arg Arg Gly Gly Thr
305                 310                 315                 320

Pro Gly His His Leu Leu Pro Leu Arg Ser Ser Ser Leu Glu Arg
                325                 330                 335

Gly Met His Met Pro Thr Ser Pro Thr Phe Leu Glu Gly Asn Thr Val
            340                 345                 350

Val
```

<210> SEQ ID NO 20
<211> LENGTH: 1343
<212> TYPE: DNA
<213> ORGANISM: Rattus sp.
<220> FEATURE:
<221> NAME/KEY: CDS
<222> LOCATION: (2)..(673)
<223> OTHER INFORMATION: "n" is residue 1325; "n" represents to C, T, G, or A

<400> SEQUENCE: 20

```
c cgt gtg tat ggc tgc atc ggt ctg tgc tgg ctg ctg gca gct acc ctg    49
  Arg Val Tyr Gly Cys Ile Gly Leu Cys Trp Leu Leu Ala Ala Thr Leu
  1               5                   10                  15 ggc ctg ctg ccc ctg ctg ggc tgg aac tgt gtg tgc gcc ttc cag cgc    97
Gly Leu Leu Pro Leu Leu Gly Trp Asn Cys Val Cys Ala Phe Gln Arg
            20                  25                  30 tgc tct agc ctg ctg ccc ctc tac tcc aag ggc tat gtg ctc ttt tgt   145
Cys Ser Ser Leu Leu Pro Leu Tyr Ser Lys Gly Tyr Val Leu Phe Cys
        35                  40                  45 gtg gtg gtc ttc gcc cta atc cta gtg act atc ctg agc ctc tac ggg   193
Val Val Val Phe Ala Leu Ile Leu Val Thr Ile Leu Ser Leu Tyr Gly
    50                  55                  60 gcc atc ttt agg gtg gtc cga gcc aac ggg cag aag tcc ccg cgt cct   241
Ala Ile Phe Arg Val Val Arg Ala Asn Gly Gln Lys Ser Pro Arg Pro
65                  70                  75                  80 cct gcc cgc cgc aag tcc cgc agg cta ctc aac acc gtg ctg atg atc   289
Pro Ala Arg Arg Lys Ser Arg Arg Leu Leu Asn Thr Val Leu Met Ile
                85                  90                  95 ttg gtg gct ttt gtg gtg tgc tgg ggt ccc ctg ttt ggc ctg ctc ctg   337
Leu Val Ala Phe Val Val Cys Trp Gly Pro Leu Phe Gly Leu Leu Leu
            100                 105                 110 gcc gac atc ttt gga tct aat gtc tgg gcc cag gag tac ctg cgc ggc   385
Ala Asp Ile Phe Gly Ser Asn Val Trp Ala Gln Glu Tyr Leu Arg Gly
        115                 120                 125 atg gac tgg atc ctg gcc cta gct gtg ctc aac tca gcc atc aat cct   433
Met Asp Trp Ile Leu Ala Leu Ala Val Leu Asn Ser Ala Ile Asn Pro
    130                 135                 140 ctc atc tat tcc ttc cgc agc cgt gag gtg cag cac gct gtg ctg acc   481
Leu Ile Tyr Ser Phe Arg Ser Arg Glu Val Gln His Ala Val Leu Thr
145                 150                 155                 160
```

-continued

```
ttc ctg tgc tgc ggc tgc ctc agg tta ggc ctg aga ggc cct gga gac      529
Phe Leu Cys Cys Gly Cys Leu Arg Leu Gly Leu Arg Gly Pro Gly Asp
            165                 170                 175 tgc ctg acc cgg atc acc gag gcc cac tct ggg gca tcc acc act gac      577
Cys Leu Thr Arg Ile Thr Glu Ala His Ser Gly Ala Ser Thr Thr Asp
        180                 185                 190 agc tcg ctg agg ccc agg gaa agt ttt cgg act tcg agg tca ctc agc      625
Ser Ser Leu Arg Pro Arg Glu Ser Phe Arg Thr Ser Arg Ser Leu Ser
    195                 200                 205 ttc aag atg cga gag ccg ctg tcc agc gtt tcc agc atc cca gcg cct      673
Phe Lys Met Arg Glu Pro Leu Ser Ser Val Ser Ser Ile Pro Ala Pro
210                 215                 220 agagcttgaa ccagccggtc gcccaccgag caggcctccc aggaaaagtt aaraaggact    733
ggamacaaga tctyagccga cagtgaytga raaatgcttg caggccccgg gttcyttcca    793
cgaaaytccc catgatgaat gttyggcagg rakkgccaga tccagatcca gtgagtctgg    853
gcctcgatgg ggctcccagg cagcaaaggg ggtktccatk tccgaggcca tggacgggac    913
agggccttac ggytatttct tagacacahk tktkctgcka ccaggaygct gyaacatgtc    973
tcttggtcac agtgctttgg gggtgtgtca ctggcacaca gtgcttcggg agtgtgctgg   1033
gawggggtac acctgcacca tttgttygaa gacaaccwga hgygtygtaa gaactacagg   1093
aggggctggg ggcaccccag tctgtcatcc attcctcttc tcagtgactt ccccaktggg   1153
acaagcaacc tgcccccatg gcctctctcc tccgggttct ctatctctct gtggggagat   1213
agacccaccc acccgaggtc tggggcaatc tcaactggtc atgtaaccct acagcctcgc   1273
ccttccggtt mtgaatcacc aagatatgct gygacaggaa gctgtggact cntacctygt   1333
gacagtacag                                                          1343
```

<210> SEQ ID NO 21
<211> LENGTH: 224
<212> TYPE: PRT
<213> ORGANISM: Rattus sp.

<400> SEQUENCE: 21

```
Arg Val Tyr Gly Cys Ile Gly Leu Cys Trp Leu Leu Ala Ala Thr Leu
 1               5                  10                  15

Gly Leu Leu Pro Leu Leu Gly Trp Asn Cys Val Cys Ala Phe Gln Arg
                20                  25                  30

Cys Ser Ser Leu Leu Pro Leu Tyr Ser Lys Gly Tyr Val Leu Phe Cys
            35                  40                  45

Val Val Val Phe Ala Leu Ile Leu Val Thr Ile Leu Ser Leu Tyr Gly
        50                  55                  60

Ala Ile Phe Arg Val Val Arg Ala Asn Gly Gln Lys Ser Pro Arg Pro
 65                  70                  75                  80

Pro Ala Arg Arg Lys Ser Arg Arg Leu Leu Asn Thr Val Leu Met Ile
                85                  90                  95

Leu Val Ala Phe Val Val Cys Trp Gly Pro Leu Phe Gly Leu Leu Leu
            100                 105                 110

Ala Asp Ile Phe Gly Ser Asn Val Trp Ala Gln Glu Tyr Leu Arg Gly
        115                 120                 125

Met Asp Trp Ile Leu Ala Leu Ala Val Leu Asn Ser Ala Ile Asn Pro
130                 135                 140

Leu Ile Tyr Ser Phe Arg Ser Arg Glu Val Gln His Ala Val Leu Thr
145                 150                 155                 160
```

-continued

```
Phe Leu Cys Cys Gly Cys Leu Arg Leu Gly Leu Arg Gly Pro Gly Asp
                165                 170                 175

Cys Leu Thr Arg Ile Thr Glu Ala His Ser Gly Ala Ser Thr Thr Asp
            180                 185                 190

Ser Ser Leu Arg Pro Arg Glu Ser Phe Arg Thr Ser Arg Ser Leu Ser
        195                 200                 205

Phe Lys Met Arg Glu Pro Leu Ser Ser Val Ser Ser Ile Pro Ala Pro
    210                 215                 220
```

We claim:

1. An isolated nucleic acid comprising a nucleotide sequence selected from the group consisting of:
   (a) a nucleotide sequence which encodes the amino acid sequence of SEQ ID NO:13; and
   (b) a complement of the nucleotide sequence (a).

2. The isolated nucleic acid of claim 1, wherein the nucleotide sequence (a) is within nucleotide sequence 13–1164, inclusive, of SEQ ID NO:12.

3. An expression vector comprising a nucleic acid according to claim 1.

4. A host cell containing the expression vector of claim 3.

5. An isolated polypeptide comprising the amino acid sequence of SEQ ID NO:13.

* * * * *